United States Patent [19]
Chucholowski et al.

[11] Patent Number: 5,521,160
[45] Date of Patent: May 28, 1996

[54] SULFURIC ACID ESTERS OF SUGAR ALCOHOLS

[75] Inventors: Alexander Chucholowski, Bad Krozingen; Jürgen Fingerle, Rheinfelden, both of Germany; Niggi Iberg, Basel, Switzerland; Hans P. Märki, Basel, Switzerland; Rita Müller, Basel, Switzerland; Michael Pech, Hartheim, Germany; Marianne Rouge, Basel, Switzerland; Gérard Schmid, Kienberg, Switzerland; Thomas Tschopp, Ettingen, Switzerland; Hans P. Wessel, Heitersheim, Germany

[73] Assignee: Hoffmann-La Roche Inc., Nutley, N.J.

[21] Appl. No.: 368,519

[22] Filed: Jan. 4, 1995

[30] Foreign Application Priority Data

Jan. 14, 1994 [CH] Switzerland ............... 114/94
Nov. 7, 1994 [CH] Switzerland ............... 3315/94

[51] Int. Cl.⁶ .................................... C07H 5/04
[52] U.S. Cl. ................. 514/42; 514/25; 514/599; 514/600; 514/601; 514/613; 514/616; 514/738; 514/739; 536/4.1; 536/22.1; 564/80; 564/123; 564/152; 564/154
[58] Field of Search ............... 514/25, 42, 599, 514/600, 601, 613, 616, 738, 739; 536/4.1, 22.1; 564/80, 123, 152, 154

[56] References Cited

U.S. PATENT DOCUMENTS 5,008,247  4/1991  Meinetsberger ............ 514/23
5,037,973  8/1991  Meinetsberger ............ 536/53
5,298,616  3/1994  Hosang et al. ............. 536/118
5,447,919  9/1995  Hosang et al. ............. 514/53

FOREIGN PATENT DOCUMENTS 312086  2/1994  European Pat. Off. .

OTHER PUBLICATIONS

Wessel et al., Carbohydrate Research, 204, pp. 131–139 (1990).

Wessel et al., Bioorganic & Medicinal Chemistry Letters, vol. 4, No. 12, pp. 1419–1423 (1994).

*Primary Examiner*—Douglas W. Robinson
*Assistant Examiner*—Kathleen Kahler Fonda
*Attorney, Agent, or Firm*—George M. Gould; William H. Epstein; Raina Semionow

[57] ABSTRACT

The present invention is concerned with novel sulfuric acid esters of sugar alcohols and sugar alcohol-like compounds of the formula

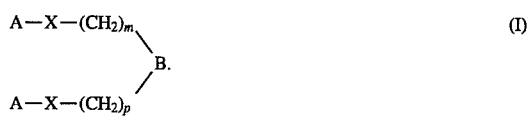

Also described are methods for the treatment and/or prophylaxis of arteriosclerotic changes in the vascular wall as well as a process for the manufacture of the compounds of formula I and their salts.

13 Claims, No Drawings

SULFURIC ACID ESTERS OF SUGAR ALCOHOLS

SUMMARY AND BACKGROUND OF THE INVENTION

The present invention is concerned with novel sulfuric acid esters of sugar alcohols and sugar alcohol-like compounds of the formula

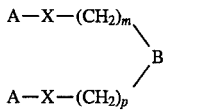

wherein

A is the residue of a sugar alcohol or of a derivative thereof that lacks the 1-hydroxy group, or the tris-(hydroxymethyl)methyl residue, with at least one hydroxy group of the residue A being esterified with sulfuric acid;

X is —$NR^1CO$—; —NHCONH—; —NHCSNH—; —$NHSO_2$—; —$NR^1$— or —O—;

m and p are each independently 0 or 1;

$R^1$ is hydrogen, lower-alkyl or hydroxy-lower-alkyl; and

B is a system of conjugated multiple bonds; and salts thereof.

Furthermore, the invention is concerned with pharmaceutical preparations containing a compound of general formula I or a salt thereof; the use of the compounds of general formula I and their salts as medicaments, especially for the treatment and/or prophylaxis of arteriosclerotic changes in the vascular wall, e.g. for the prevention of restenosis after coronary or peripheral angioplasty or after bypass operations; for the production of medicaments for the said indications; as well as a process for the manufacture of the compounds of general formula I and their salts.

DETAILED DESCRIPTION OF THE INVENTION

The present invention is concerned with novel sulfuric acid esters of sugar alcohols and sugar alcohol-like compounds of the general formula

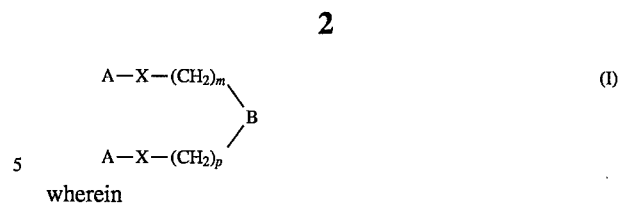

wherein

A is the residue of a sugar alcohol or of a derivative thereof that lacks the 1-hydroxy group, or the tris-(hydroxymethyl)methyl residue, with at least one hydroxy group of the residue A being esterified with sulfuric acid;

X is —$NR^1CO$—; —NHCONH—; —NHCSNH—; —$NHSO_2$—; —$NR^1$— or —O—;

m and p are each independently 0 or 1;

$R^1$ is hydrogen, lower-alkyl or hydroxy-lower-alkyl;

B is a system of conjugated multiple bonds;

and salts thereof.

Preferably, the residue A of a sugar alcohol that lacks the 1-hydroxy group is a residue —$(CHR^2)_nCH_2R^2$ and n is a whole number of 1–5; $R^2$ is H, —$OSO_3H$ or OZ; Z is a protecting group; and at least one residue $R^2$ is —$OSO_3H$.

Examples of sugar alcohols from which residue A is derived are hexitols, such as glucitol, galactitol, mannitol and gulitol, and pentitols, such as arabinitol, ribitol and xylitol. Examples of derivatives of such sugars are mono- or multiply-deoxygenated sugar alcohols, such as L-rhamnitol. These sugar alcohols can be present in the D- or L-form or as a racemate, with the naturally occurring form or the form which corresponds to the parent, naturally occurring sugar being preferred.

Preferably, the conjugated multiple bonds are conjugated double bonds.

Examples of systems of conjugated double bonds are polyene hydrocarbon residues having 3–8 conjugated double bonds, e.g. octa-2,4,6-triene-2,7-diyl and 6,11-dimethyl-hexadeca-2,4,6,8,10,12,14-heptaene- 2,15-diyl; and aromatic ring systems, especially phenylene, phenylene substituted by lower-alkyl, naphthylene or fluorenylene, or those of formulae (a) to (s) below:

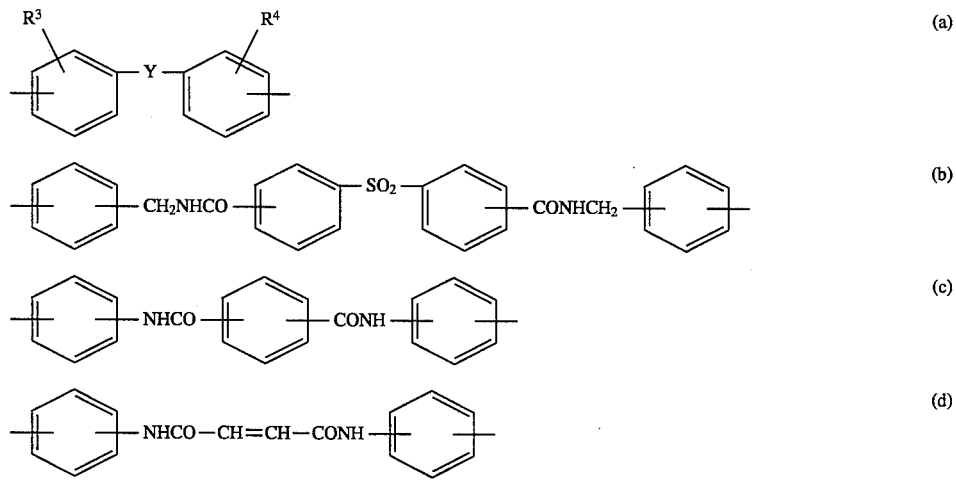

-continued
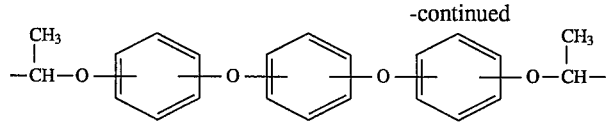 (e)
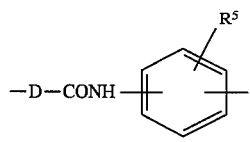 (f)
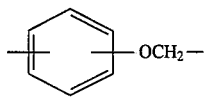 (g)
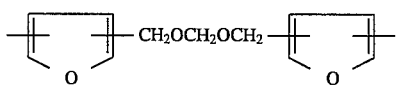 (h)
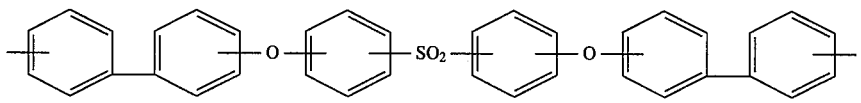 (i)
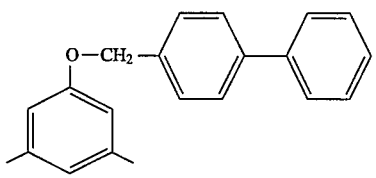 (j)
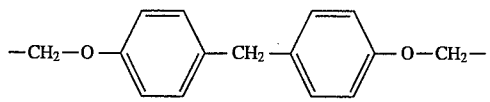 (k)
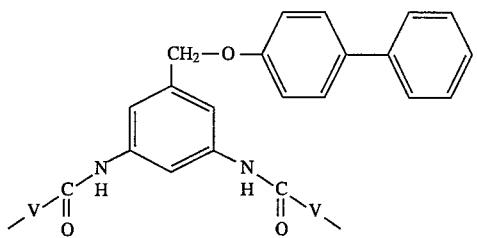 (l)
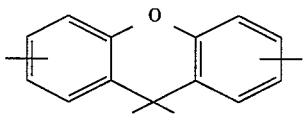 (m)
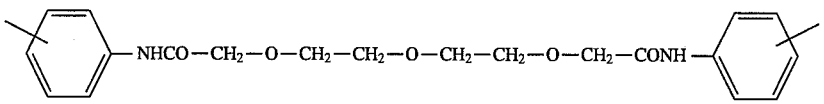 (n)
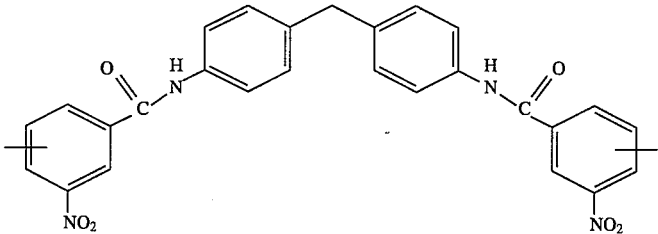 (o)

-continued

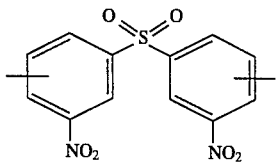
(p)

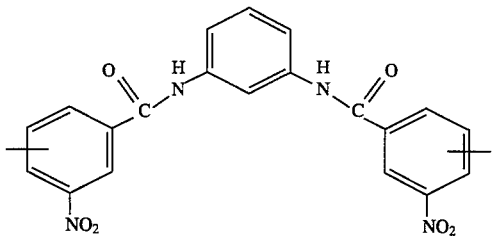
(q)

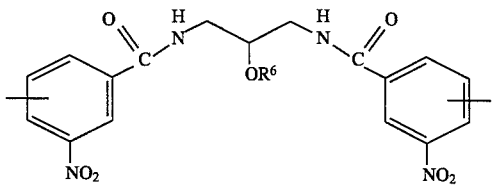
(r)

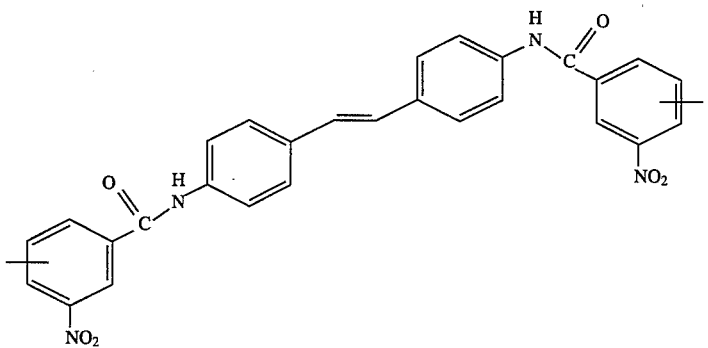
(s)

wherein Y is a carbon-carbon bond, —O—, —CO—, —CH$_2$—, —CH$_2$CH$_2$—, —CH=CH—, —C≡C—, —CH(O)CH—, —SO$_2$—, —C(CF$_3$)$_2$—, —CONR$^1$—, —NHCONH—, —NHCOCONH—, phenylene or phenylenedioxy; R$^1$ is hydrogen, lower-alkyl or hydroxy-lower-alkyl; R$^3$ and R$^4$ are hydrogen, lower-alkyl, lower-alkoxy, halogen or —SO$_3$H; R$^5$ is lower-alkoxy-lower-alkoxy, phenoxy or phenoxy substituted by halogen; R$^6$ is hydrogen or SO$_3$H; D is —CH$_2$CH$_2$— or —CH=CH— and V is —CH=CH—, CH$_2$CH$_2$ or a single bond.

The term "lower", e.g."lower alkyl", as used herein, denotes groups with 1–6 C atoms, such as methyl, ethyl, propyl, butyl and, respectively, methoxy, ethoxy, propoxy and butoxy.

"Halogen" embraces fluorine, chlorine, bromine and iodine, of which chlorine is preferred.

"Phenylene" residues are preferably 1,3- and 1,4-phenylene residues.

"Naphthylene" residues are preferably 1,4-, 1,5- and 2,6-naphthylene residues.

2,7-Fluorenylene is a preferred fluorenylene residue.

In formulae (a) to (i) the bonds emanating from the rings are preferably in the p-position to each other.

Examples of salts of compounds of general formula I are alkali metal salts, such as Na or K salts, ammonium salts and salts of tertiary amines, such as triethylamine, or pyridinium or imidazolium salts, or quaternary ammonium salts, such as dodecyl-trimethylammonium, ethylpyridinium and benzethonium salts; as well as alkaline earth metal salts, such as Ca or Mg salts.

Examples of representative compounds in which the aromatic ring system is a residue of formula (a) are:

(E)-Stilbene-4,4'-dicarboxylic acid bis-(2,3,4,5,6-penta-O-sulfo-D-glucit-1-ylamide) decasodium salt,
(Z)-stilbene-4,4'-dicarboxylic acid bis-(2,3,4,5,6-penta-O-sulfo-D-glucit-1-ylamide) decasodium salt,
4,4'-sulfonyl-dibenzoic acid bis-(2,3,4,5,6-penta-O-sulfo-D-glucit-1-ylamide) decasodium salt,
4,4'-ethylene-dibenzoic acid bis-(2,3,4,5,6-penta-O-sulfo-D-glucit-1-ylamide) decasodium salt,
4,4'-carbonyl-dibenzoic acid bis-(2,3,4,5,6-penta-O-sulfo-D-glucit-1-ylamide) decasodium salt,
4,4'-methylene-dibenzoic acid bis-(2,3,4,5,6-penta-O-sulfo-D-glucit-1-ylamide) decasodium salt,
4,4'-oxy-dibenzoic acid bis-(2,3,4,5,6-penta-O-sulfo-D-glucit-1-ylamide) decasodium salt,
4,4'-(hexafluoro-propane-2,2-diyl)-dibenzoic acid bis-(2,3,4,5,6-penta-O-sulfo-D-glucit-1-ylamide) decasodium salt,
biphenyl-4,4'-dicarboxylic acid bis-(2,3,4,5,6-penta-O-sulfo-D-glucit-1-ylamide) decasodium salt,
3,3'-bis-(2,3,4,5,6-penta-O-sulfo-D-glucit-1-yl)-1,1'-(3,3'-dichloro-4,4'-methylene-diphenyl)-diurea decasodium salt,
3,3'-bis-(2,3,4,5,6-penta-O-sulfo-D-glucit-1-yl)-1,1'-(3,3'-dimethyl-biphenyl- 4,4'-diyl)-diurea decasodium salt,
3,3'-bis-(2,3,4,5,6-penta-O-sulfo-D-glucit-1-yl)-1,1'-(3,3'-dimethoxy-biphenyl- 4,4'-diyl)-diurea decasodium salt, 3,3'-bis-(2,3,4,5,6-penta-O-sulfo-D-glucit-1-yl)-1,1'-(3,3'-dichloro-biphenyl- 4,4'-diyl)-diurea decasodium salt, 1,1'-(4,4'-methylene-diphenyl)-3,3'-bis-(2,3,4,5,6-penta-O-sulfo-D-glucit-1-yl)-diurea decasodium salt, (E)-4,4'-bis-[3-(2,3,4,5,6-penta-O-sulfo-D-glucit-1-yl)-thioureido]-stilbene-2,2'-disulfonic acid dodecasodium salt, biphenyl-4,4'-disulfonic acid bis-(2,3,4,5,6-penta-O-sulfo-D-glucit-1-ylamide) decasodium salt, 4,4'-oxy-dibenzenesulfonic acid bis-(2,3,4,5,6-penta-O-sulfo-D-glucit-1-ylamide) decasodium salt, 1,3-bis-[4-(2,3,4,5-tetra-O-sulfo-D-arabinit-1-yloxy)-phenyl]-urea octasodium salt, N'-methyl-N-(2,3,4,5,6-penta-O-sulfo-D-glucit-1-yl)-N'-[4-(2,3,4,5,6-penta-O-sulfo-D-glucit- 1-ylcarbamoyl)-phenyl]-terephthalamide decasodium salt, N-(2,3,4,5,6-penta-O-sulfo-D-glucit-1-yl)-N'-[4-(2,3,4,5,6-penta-O-sulfo-D-glucit- 1-ylcarbamoyl)-phenyl]-terephthalamide decasodium salt, N,N'-bis-[4-[3-(2,3,4,5,6-penta-O-sulfo-D-glucit-1-yl)-ureido]-phenyl]-oxalamide decasodium salt, Z-stilbene-4,4'-dicarboxylic acid bis-(2-hydroxysulfonyloxy-1,1-bis-hydroxysulfonyloxymethyl-ethylamide) hexasodium salt, 4,4'-ethynylenedibenzoic acid bis-(2,3,4,5,6-penta-O-sulfo-D-glucit-1-ylamide) decasodium salt, 2,2',3,3',4,4',5,5'-octa-O-sulfo-1,1'-O-(4,4'-ethynediyl-diphenylene)-di-D-arabinitol octasodium salt, 2,2',3,3',4,4',5,5'-octa-O-sulfo-1,1'-biphenyl-4,4'-diyl-di-D-arabinitol octasodium salt, (Z)-2,2',3,3',4,4',5,5'-octa-O-sulfo-1,1'-O-(4,4'-ethylene-diphenylene)-di-D-arabinitol octasodium salt, 2,2',3,3',4,4',5,5'-octa-O-sulfo-1,1'-O-(4,4'-ethane-1,2-diyl-diphenylene)-di-D-arabinitol octasodium salt, 1,3-bis-[4-(2,3,4,5,6-penta-O-sulfo-D-galactit-6-yloxy)-phenyl]-urea decasodium salt, cis-4,4'-oxiran-2,3-diyl-dibenzoic acid bis-(2,3,4,5,6-penta-O-sulfo-D-glucit-1-ylamide) decasodium salt (E)-stilbene-3,4'-dicarboxylic acid bis-(2,3,4,5,6-penta-O-sulfo-D-glucit-1-ylamide) decasodium salt, (E)-stilbene-3,3'-dicarboxylic acid bis-(2,3,4,5,6-penta-O-sulfo-D-glucit-1-ylamide) decasodium salt, (E)-stilbene-2,4'-dicarboxylic acid bis-(2,3,4,5,6-penta-O-sulfo-D-glucit-1-ylamide) decasodium salt, (E)-stilbene-2,3'-dicarboxylic acid bis-(2,3,4,5,6-penta-O-sulfo-D-glucit-1-ylamide) decasodium salt, (Z)-stilbene-2,2'-dicarboxylic acid bis-(2,3,4,5,6-penta-O-sulfo-D-glucit-1-ylamide) decasodium salt, (Z)-stilbene-3,4'-dicarboxylic acid bis-(2,3,4,5,6-penta-O-sulfo-D-glucit-1-ylamide) decasodium salt, (Z)-stilbene-3,3'-dicarboxylic acid bis-(2,3,4,5,6-penta-O-sulfo-D-glucit-1-ylamide) decasodium salt, (Z)-stilbene-2,3'-dicarboxylic acid bis-(2,3,4,5,6-penta-O-sulfo-D-glucit-1-ylamide) decasodium salt, 3,4'-ethylenedibenzoic acid bis-(2,3,4,5,6-penta-O-sulfo-D-glucit-1-ylamide) decasodium salt, 2,4'-ethylenedibenzoic acid bis-(2,3,4,5,6-penta-O-sulfo-D-glucit-1-ylamide) decasodium salt, 2,3'-ethylenedibenzoic acid bis-(2,3,4,5,6-penta-O-sulfo-D-glucit-1-ylamide) decasodium salt, 2,2'-ethylenedibenzoic acid bis-(2,3,4,5,6-penta-O-sulfo-D-glucit-1-ylamide) decasodium salt, 3,3'-ethylenedibenzoic acid bis-(2,3,4,5,6-penta-O-sulfo-D-glucit-1-ylamide) decasodium salt, (E)-2-chlorostilbene-4,4'-dicarboxylic acid bis-(2,3,4,5,6-penta-O-sulfo-D-glucit-1-ylamide) decasodium salt, (Z)-2-chlorostilbene-4,4'-dicarboxylic acid bis-(2,3,4,5,6-penta-O-sulfo-D-glucit-1-ylamide) decasodium salt, (E)-2-bromostilbene-4,4'-dicarboxylic acid bis-(2,3,4,5,6-penta-O-sulfo-D-glucit-1-ylamide) decasodium salt, (Z)-2-bromostilbene-4,4'-dicarboxylic acid bis-(2,3,4,5,6-penta-O-sulfo-D-glucit-1-ylamide) decasodium salt, (Z)-stilbene-4,4'-dicarboxylic acid bis-(2,3,4,5,6-penta-O-sulfo-D-mannit-1-ylamide) decasodium salt, (Z)-stilbene-4,4'-dicarboxylic acid bis-(2,3,4,5,6-penta-O-sulfo-D-galactit-1-ylamide) decasodium salt, (Z)-stilbene-4,4'-dicarboxylic acid bis-(2,3,4,5,6-penta-O-sulfo-D-arabinit-1-ylamide) octasodium salt, (Z)-stilbene-4,4'-dicarboxylic acid bis-(2,3,4,5,6-penta-O-sulfo-L-rhamnit-1-ylamide) octasodium salt.

Examples of representative compounds in which the aromatic ring system is naphthylene or fluorenylene are:

Naphthalene-2,6-dicarboxylic acid bis-(2,3,4,5,6-penta-O-sulfo-D-glucit-1-ylamide) decasodium salt, naphthalene-1,5-disulfonic acid bis-(2,3,4,5,6-penta-O-sulfo-D-glucit-1-ylamide) decasodium salt, naphthalene-1,4-dicarboxylic acid bis-(2,3,4,5,6-penta-O-sulfo-D-glucit-1-ylamide) decasodium salt, 9-oxo-9H-fluorene-2,7-dicarboxylic acid bis-(2,3,4,5,6-penta-O-sulfo-D-glucit-1-ylamide) decasodium salt, 9-oxo-9H-fluorene-2,7-dicarboxylic acid bis-[methyl-(2,3,4,5,6-penta-O-sulfo-D-glucit-1-yl)-amide] decasodium salt.

Examples of representative compounds in which the aromatic ring system is phenylene or phenylene substituted by lower-alkyl are:

3,3'-bis-(2,3,4,5,6-penta-O-sulfo-D-glucit-1-yl)-1,1'-(benzene-1,4-diyl)-dithiourea decasodium salt, 3,3'-bis-(2,3,4,5,6-penta-O-sulfo-D-glucit-1-yl)-1,1'-(benzene-1,4-diyl)-dithiourea decasodium salt, N,N'-bis-(2,3,4,5,6-penta-O-sulfo-D-glucit-1-yl)-terephthalamide decasodium salt, N,N'-bis-(2,3,4,5,6-penta-O-sulfo-D-glucit-1-yl)-isophthalamide decasodium salt, 3,3'-bis-(2,3,4,5,6-penta-O-sulfo-D-glucit-1-yl)-1,1'-(toluene-2,6-diyl)-diurea decasodium salt, 3,3'-bis-(2,3,4,5,6-penta-O-sulfo-D-glucit-1-yl)-1,1'-(benzene-1,3-diyl-dimethylene)-diurea decasodium salt, N,N'-dimethyl-N,N'-bis-(2,3,4,5,6-penta-O-sulfo-D-glucit-1-yl)-terephtalamide decasodium salt, 3,3'-dimethyl-3,3'-bis-(2,3,4,5,6-penta-O-sulfo-D-glucit-1-yl)-1,1'-(toluene-2,6-diyl)-diurea decasodium salt, 3,3'-bis-(2,3,4,5,6-penta-O-sulfo-D-mannit-1-yl)-1,1'-(toluene-2,6-diyl)-diurea decasodium salt, 3,3'-bis-(2,3,4,5,6-penta-O-sulfo-D-galactit-1-yl)-1,1'-(toluene-2,6-diyl)-diurea decasodium salt, 3,3'-bis-(2,3,4,5,6-penta-O-sulfo-D-arabinit-1-yl)-1,1'-(toluene-2,6-diyl)-diurea octasodium salt, 3,3'-bis-(2,3,4,5,6-penta-O-sulfo-L-rhamnit-1-yl)-1,1'-(toluene-2,6-diyl)-diurea octasodium salt.

Examples of representative compounds in which the aromatic ring system is a residue of formula (b)–(s) are:

4,4'-Sulfonyl-dibenzoic acid bis-[4-(2,3,4,5,6-penta-O-sulfo-D-glucit-1-ylcarbamoyl)-benzylamide] decasodium salt, formula b)

N,N'-bis-[4-[3-(2,3,4,5,6-penta-O-sulfo-D-glucit-1-yl)-ureido]-phenyl]-isophthalamide decasodium salt, formula c)

N,N'-bis-[4-(2,3,4,5-tetra-O-sulfo-D-arabinit-1-yloxy)-phenyl]-isophthalamide octasodium salt, formula c)

N,N'-bis-[4-[3-(2,3,4,5,6-penta-O-sulfo-D-glucit-1-yl)-ureido]-phenyl]-isophthalamide decasodium salt, formula c)

N,N'-bis-[4-(2,3,4,5-tetra-O-sulfo-D-arabinit-1-yloxy)-phenyl]-terephthalamide octasodium salt, formula c)

N,N'-bis-[4-[3-(2,3,4,5,6-penta-O-sulfo-D-glucit-1-yl)-ureido]-phenyl]-fumaramide decasodium salt, formula d)

2-[4-[4-[4-[1-(2,3,4,5,6-penta-O-sulfo-D-glucit-1-ylcarbamoyl)-ethoxy]-phenoxy]-phenoxy]-phenoxy]-propionic acid 2,3,4,5,6-penta-O-sulfo-D-glucit-1-ylamide decasodium salt, formula e)

(Z)-but-2-enedicarboxylic acid 1-[4-(4-chloro-phenoxy)-3-(2,3,4,5,6 -penta-O-sulfo-D-1-glucit-1-ylcarbamoyl)-phenyl]-amide 4-(2,3,4,5,6-penta-O-sulfo-D-glucit-1-yl)-amide decasodium salt, formula f)

N1-[4-(4-chloro-phenoxy)-3-(2,3,4,5,6-penta-O-sulfo-D-glucit-1-ylcarbamoyl)-phenyl]-N4-( 2,3,4,5,6-penta-O-sulfo-D-glucit-1-yl)succinamide decasodium salt, formula f)

(Z)-but-2-enedicarboxylic acid 1-(2,3,4,5,6-penta-O-sulfo-D-glucit-1-yl)-amide 4-[4-(2-methoxy-ethoxy)-3-(2,3,4,5,6-penta-O-sulfo-D-glucit-1-ylcarbamoyl)-phenyl]-amide decasodium salt, formula f)

N1-[4-(2-methoxy-ethoxy)-3-(2,3,4,5,6-penta-O-sulfo-D-glucit-1-ylcarbamoyl)-phenyl]-N4-( 2,3,4,5,6-penta-O-sulfo-D-glucit-1-yl)succinamide decasodium salt, formula f)

N-(2,3,4,5,6-penta-O-sulfo-D-glucit-1-yl)-4-(2,3,4,5,6-penta-O-sulfo-D-glucit- 1-ylcarbamoylmethoxy)-benzamide decasodium salt, formula g)

5,5'-(methylene-bis-oxymethylene)-di-furan-2-carboxylic acid bis-(2,3,4,5,6-penta-O-sulfo-D-glucit-1-yl-amide) decasodium salt, formula h)

4'-[4-[4-[4'-(2,3,4,5,6-penta-O-sulfo-D-glucit-1-ylcarbamoyl)-biphenyl-4-yloxy]-phenylsulfonyl]-phenoxy]-biphenyl-4-carboxylic acid 2,3,4,5,6-penta-O-sulfo-D-glucit-1-ylamide decasodium salt, formula i)

5-biphenyl-4-ylmethoxy-N,N'-bis-(2,3,4,5,6-penta-O-sulfo-D-glucit-1-yl)-isophthalamide decasodium salt, formula j)

N-(2,3,4,5,6-penta-O-sulfo-D-glucit-1-yl)-2-[4-[4-(2,3,4,5,6-penta-O-sulfo-D-glucit- 1-ylcarbamoylmethoxy)-benzyl]-phenoxy]-acetamide decasodium salt, formula k)

(Z)-butenedioic acid (Z)-[3-biphenyl-4-yloxymethyl-5-[3-(2,3,4,5,6-penta-O-sulfo-D-glucit- 1-ylcarbamoyl)-acryloylamino]-phenylamide]-(2,3,4,5,6-penta-O-sulfo-D-glucit-1-yl)-amide decasodium salt, formula l)

N1-[3-biphenyl-4-yloxymethyl-5-[3-(2,3,4,5,6-penta-O-sulfo-D-glucit- 1-ylcarbamoyl)-propionylamino]-phenyl]-N4-(2,3,4,5,6-penta-O-sulfo-D-glucit-1-yl)-succinamide decasodium salt, formula l)

3,3'-bis-(2,3,4,5,6-penta-O-sulfo-D-glucit-1-yl)-1,1'-(5-biphenyl-4-yloxymethyl-benzene-1,3-diyl)-diurea decasodium salt, formula l)

2,2',3,3',4,4',5,5'-octa-O-sulfo-1,1'-O-(9,9-dimethyl-9H-xanthene-3,6-diyl)-di-D-arabinitol octasodium salt, formula m)

3,6,9-trioxaundecanedioic acid bis-[4-(2,3,4,5-tetra-O-sulfo-D-arabinit-1-yloxy)phenylamide] octasodium salt, formula n)

4,4'-bis-(2,3,4,5,6-penta-O-sulfo-D-glucit-1-ylamino)-3,3'-dinitro-N,N'-( 4,4'-methylene-diphenyl)-dibenzamide decasodium salt, formula o)

N,N'-bis-(2,3,4,5,6-penta-O-sulfo-D-glucit-1-yl)-2,2'-dinitro-4,4'-sulfonyldianiline decasodium salt, formula p)

4,4'-bis-(2,3,4,5,6-penta-O-sulfo-D-glucit-1-ylamino)-3,3'-dinitro-N,N'-benzene- 1,3-diyl-dibenzamide decasodium salt, formula q)

4,4'-bis-(2,3,4,5,6-penta-O-sulfo-D-glucit-1-ylamino)-3,3'-dinitro-N,N'-(2-hydroxysulfonyloxy-propane-1,3-diyl)-dibenzamide undecasodium salt, formula r)

(E)-4,4'-bis-(2,3,4,5,6-penta-O-sulfo-D-glucit-1-ylamino)-3,3'-dinitro-N,N'-stilbene- 4,4'-diyl-dibenzamide decasodium salt, formula s).

Examples of representative compounds in which the system of conjugated multiple bonds B is a polyene hydrocarbon are:

(2E,4E,6E,8E,10E,12E,14E)-2,6,11,15-Tetramethyl-hexadeca-2,4,6,8,10,12,14-heptaenedicarboxylic acid bis-(2,3,4,5,6-penta-O-sulfo-D-glucit-1-ylamide) decasodium salt, (2E,4E,6E)-2,7-dimethyl-octa-2,4,6-trienedicarboxylic acid bis-(2,3,4,5,6-penta-O-sulfo-D-glucit-1-ylamide) decasodium salt.

A system of conjugated triple bonds is, for example, a polyyne hydrocarbon residue having 2 conjugated triple bonds; a representative of such a compound being, for example, 2,2',3,3',4,4',5,5'-octa-O-sulfo-1,1'-O-hexa-2,4-diyne-1,6-diyl-di-D-arabinitol octasodium salt.

The compounds of formula I are manufactured by reacting a non-sulfated compound of general formula I with a sulfating agent.

The sulfation in accordance with the present invention is carried out by known methods for the sulfation of hydroxy groups. Examples of sulfating agents are $SO_3$ complexes, such as $SO_3$.pyridine, $SO_3$.trimethylamine, $SO_3$.dioxane and $SO_3$.dimethylformamide. Further examples of sulfating agents are chlorosulfonic acid, mixtures of chlorosulfonic acid and sulfuric acid, and piperidine N-sulfate.

The reaction is conveniently effected in a suitable solvent, especially a polar solvent, e.g. dimethylformamide, dimethyl sulfoxide or hexamethylphosphortriamide. The reaction can be carried out at room temperature or at an elevated temperature, e.g. at 20°–70° C., whereby the degree of sulfation is influenced by varying the reaction duration and temperature. The degree of sulfation achieved in each case can be determined by HPLC. In a preferred embodiment all or practically all free hydroxy groups are sulfated by suitable choice of reaction duration and temperature. The working-up of the reaction mixture and, respectively, the isolation of the reaction product of formula I are effected according to known methods, e.g. by gel filtration or ultrafiltration. Conveniently, the reaction mixture is treated, prior to the working-up, with a compound which is sufficiently basic to form a salt with the sulfonic acid groups in the compound of formula I, e.g. with an alkali metal acetate, such as sodium acetate, and the compound of formula I is isolated in salt form, e.g. as the sodium salt.

The starting materials for the process in accordance with the invention, i.e. the non-sulfated compounds corresponding to the compounds of formula I, are prepared as described in the Examples hereinafter or in analogy thereto. The starting materials for compounds of formula I are prepared in general as follows:

When $X=-NR^1CO-$, a suitable glycamine, i.e. a 1-amino-1-desoxy derivative of a sugar, a corresponding $R^1$-substituted glycamine or tris-(hydroxymethyl)-methylamine can be reacted with a suitable carboxylic acid. For this purpose, the carboxylic acid is activated using methods known in peptide chemistry, such as a mixed anhydride or as an active ester. In certain cases a simple ester or a lactone is used for the coupling.

$R^1$-Substituted glycamines can be reacted directly or glycamines can be coupled and subsequently derivatized with $R^1$.

Urea or thiourea derivatives, wherein $X=-NHCONH-$ or $-NHCSNH-$, are obtained directly by reacting an isocyanate or isothiocyanate with a suitable glycamine, a corresponding substituted glycamine or tris-(hydroxymethyl)-methylamine.

Sulfonamides, wherein $X=-NHSO_2-$, are in principle accessible by reacting an activated sulfonyl compound $-SO_2Z$, e.g. a sulfonyl chloride, with a suitable glycamine, a corresponding substituted glycamine or tris-(hydroxymethyl)-methylamine.

Analogous ethers, wherein $X=-O-$, are obtainable using known ether formation methods by reacting a glycitol with a phenol or a benzylic or allylic alcohol. After ether formation, one of the hydroxyl groups can be activated (e.g. according O. Mitsunobu, Synthesis vol. 12, P. 1, 1981) or it can be reacted as an activated hydroxyl equivalent, e.g. an allyl or benzyl halide. Amino compounds, wherein X=—NR$^1$—, are obtainable by known methods, for example by reacting an aminoglycitol with an activated aromatic compound.

The aromatic compounds of the present invention inhibit the migration and proliferation of smooth muscle cells of the vascular wall. They are thus useful in the therapy and/or prophylaxis of arteriosclerotic changes of the vascular wall, especially for the prevention of restenosis after coronary or peripheral angioplasty or after bypass operations.

In contrast to heparin, these compounds have no AT$_{III}$ activity (antithrombin III) and therefore no inhibiting effect on coagulation factors IIa and Xa. Accordingly, their blood coagulation-inhibiting activity is very much lower than that of heparin and thus the risk of bleeding in the case of therapy with these compounds is minimal.

In addition, heparin-binding proteins are known to play an important role in various known illnesses. Thus, heparin-like substances, such as the compounds mentioned in this patent are also useful for the treatment of such illnesses. Infection, for example, by Herpes and HIV is inhibited by such compounds. Similarly, arterial thrombosis, e.g. vWF and platelet adhesion, is inhibited by such compounds. In addition, activation of the complementary system, for example in the case of reperfusion, is diminished and various growth factors or cytokines, such as bFGF in tumours, are inhibited by such compounds.

The pharmacological activities of the compounds in accordance with the invention are conclusively demonstrated in the test procedures described hereinafter:

Antiproliferative activity

The antiproliferative activity of a substance is expressed as the r$_i$ value which is a comparative value to the corresponding activity of heparin and which was determined in cell cultures as follows: rat smooth muscle cells were applied to cell culture plates in a density of 8×10$^3$ cells/well (medium: DMEM with 10% FCS. Cultivation at 37° C. and 5% CO$_2$). After 4 hours the number of adhered cells was determined and the compounds to be tested (100 µg/ml, dissolved in H$_2$O) were added. The controls were a) cells to which test compound was not added and b) heparin (100 µg/ml). Subsequently, the cells were incubated for 48 hours and thereafter the cell count was determined once more.

The inhibition i of the cell growth, i.e. the percent reduction in the growth rate of the cells compared to the control, was calculated from these values:

$$i = 100 - \frac{\mu_{substance}}{\mu_{control}} \cdot 100$$

the growth rate µ being calculated as $$\mu = \frac{\Delta \ln Z}{\Delta t_{[d]}} = \ln \frac{Z_{(t2)}}{Z_{(t1)}} * \frac{1}{\Delta t_{[d]}} \; [d^{-1}]$$

in which Z is the number of cells.

Finally, r$_i$—the relative inhibitory activity—which expresses the activity of a substance (at 100 µg/ml) in comparison to the activity of heparin in the same concentration in the same experiment, was calculated:

$$r_i = \frac{i_{substance}}{i_{heparin}}$$

Blood coagulation inhibition

The blood coagulation-inhibiting activity was determined as follows:

Inhibition of Thrombin or Factor Xa in the Chromogenic Substrate Assay (Teien. et al., Thrombosis Research 10, 399–410 (1977)): The determination was effected in a Cobas-Bio centrifugal automatic spectrophotometer. The buffer solution used consisted of 50 mM Tris buffer, 180 mM NaCl, 7.5 mM EDTA Na$_2$, 1% PEG 6000 and 0.02% Tween 80, pH 8.4. The test solution consisted of 50 µl of buffer, 30 µl of antithrombin III (1 U/ml, Kabi Diagnostica) and 20 µl of plasma which contained various concentrations of test compounds. 30 µl of sample solution and 20 µl of water with 180 µl of thrombin (1 U/ml, Thrombin Reagent Roche Basle) were added to the test cuvette in the automatic analyzer. After incubation at 37° C. for 240 seconds, 60 µl of S-2238 (H-D-Phe-Pip-Arg-NH.pNA, Kabi Diagnostica, Möndal, Sweden, 0.75 mM in water) and 20 µl of water were added. The liberation of pNA (p-nitroaniline) was followed during 60 seconds at 405 nm in 10 second intervals in comparison to water as the blank. The inhibitory activity is given as the IC$_{50}$, which is the concentration [µg/ml] at which the amidolytic activity of thrombin is reduced by 50% in comparison to the plasma control value.

The inhibition of Factor Xa was measured in the same manner using a solution of Factor Xa (2.8 nkat/ml) and 2 mM S-2222 (Bz-CO-Ile-Glu-Arg-NH.pNA, Kabi Diagnostica) in water in place of thrombin or S-2238.

The activity data obtained in the previously described test procedures with a representative number of compounds of formula I are given in the following Table:

| Example | Antiproliferative Activity ri | Anticoagulative Activity IC$_{50}$ [µg/ml] | |
|---|---|---|---|
| | | Thrombin | Factor Xa |
| 1 | 0.6 | >1000 | >1000 |
| 3 | 1.5 | >1000 | >1000 |
| 4 | 0.3 | >1000 | >1000 |
| 6 | 1.5 | >1000 | >1000 |
| 10 | 1.5 | >1000 | >1000 |
| 11 | 1.0 | >1000 | >1000 |
| 12 | 0.9 | >1000 | >1000 |
| 14 | 0.6 | >1000 | >1000 |
| 16 | 0.7 | >1000 | >1000 |
| 26 | 1.5 | >1000 | >1000 |
| 33 | 0.8 | >1000 | >1000 |
| 34 | 0.4 | >1000 | >1000 |
| 37 | 0.7 | >1000 | >1000 |
| 58 | 2.2 | >1000 | >1000 |
| 65 | 0.8 | >1000 | >1000 |
| 67 | 1.0 | >1000 | >1000 |
| 68 | 1.1 | >1000 | >1000 |
| 85 | 2.1 | >1000 | >1000 |
| 93 | 1.0 | >1000 | >1000 |
| Heparin | 1.0 | 1.9 | 2.7 |

The test results show that the compounds of the present invention have an antiproliferative activity comparable to or greater than that of heparin, but in contrast to heparin, do not exhibit or exhibit a much lower, anti-coagulation activity.

The medicaments based on the compounds in accordance with the invention are administered enterally, e.g. orally in the form of tablets, coated tablets, dragées, hard and soft gelatine capsules, solutions, emulsions or suspensions, or rectally, e.g. in the form of suppositories. However, the administration is preferably effected parenterally, e.g. in the form of injection solutions.

For the production of tablets, coated tablets, dragées and hard gelatine capsules the active ingredient is mixed with pharmaceutically inert, inorganic or organic excipients. Lactose, corn starch or derivatives thereof, talc, stearic acid or its salts are used e.g. as such excipients for tablets, dragées and hard gelatine capsules. Suitable excipients for soft gelatine capsules are e.g. vegetable oils, waxes, fats, semi-solid and liquid polyols; depending on the nature of the active ingredient no excipients are, however, usually required in the case of soft gelatine capsules. Suitable excipients for the production of solutions and syrups are e.g. water, polyols, saccharose, invert sugar and glucose, suitable excipients for injection solutions are e.g. water, alcohols, polyols, glycerine and vegetable oils and suitable excipients for suppositories are e.g. natural or hardened oils, waxes, fats and semi-liquid or liquid polyols.

The pharmaceutical preparations also contain preservatives, solubilizers, stabilizers, wetting agents, emulsifiers, sweeteners, colorants, flavorants, salts for varying the osmotic pressure, buffers, coating agents or antioxidants. In the case of enteral administration the resorption of the active ingredient is increased with the aid of liposomes.

The dosage of the active ingredient varies within wide limits and will, of course, be fitted to the individual requirements in each particular case. In general, in the case of parenteral administration a dosage of about 0.1 to 100 mg/kg, preferably of about 1.5 to 15 mg/kg, per day should be appropriate for adults, although the upper limit just given can also be exceeded when this is shown to be indicated.

EXAMPLES

The present invention is illustrated further by the following non-limiting examples.

Example 1

A. A suspension of 4.33 g naphthalene-2,6-dicarboxylic acid in 5 ml of water and 20 ml of acetone was treated at 0°–5° C. over 15 minutes with 6.2 ml of triethylamine in 50 ml of acetone. 4.8 g of ethyl chloroformate in 30 ml of acetone were then added at −5°–0° C. A solution of 8.33 g of D-glucamine (1-amino-1-desoxy-glucitol) in 50 ml of water was added dropwise at 0°–5° C. during 20 minutes. After stirring at room temperature, for 20 hours the mixture was heated to 50° C. for 2 hours. The reaction mixture was evaporated, acetylated with acetic anhydride in pyridine for 17 hours at room temperature and again evaporated. The residue was extracted with ice-water and worked-up with methylene chloride. The organic phase was washed with sodium hydrogen carbonate solution and water, dried over magnesium sulfate and evaporated. The residue was chromatographed over silica gel. The product fractions were taken up in methylene chloride and treated with methanol for crystallization. The colourless crystals were filtered off under suction and washed with methanol and cold ether. A suspension of 5.0 g of this product in 75 ml of dioxan and 50 ml of methanol was treated with 3 ml of a freshly prepared sodium methylate solution (2% Na in methanol) and stirred at room temperature for 5 hours and subsequently while cooling with ice for 20 minutes. The precipitate of naphthalene-2,6-dicarboxylic acid bis-D-glucit-1-ylamide was filtered off under suction, washed with methanol/dioxane 1:1 and dried, $[\alpha]_D^{20}$ −14° (c 0.5; dimethyl sulfoxide), MS: m/z 543.4 ([M+H]$^+$).

B. A suspension of 1.1 g of naphthalene-2,6-dicarboxylic acid bis-D-glucit-1-ylamide and 5.6 g of sulfur trioxide trimethylamine complex in 20 ml of absolute dimethylformamide was stirred at 70°–75° C. for 22 hours. After cooling the mixture was treated with 6.56 g of sodium acetate in 50 ml of water and evaporated. The residue was taken up in water and the pH value was adjusted to 7–8 with dilute sodium hydroxide solution. The solution was evaporated and purified in distilled water by gel filtration (Sephadex® LH 20). The product fractions were lyophilized and gave naphthalene-2,6-dicarboxylic acid bis-(2,3,4,5,6-penta-O-sulfo-D-glucit-1-ylamide) decasodium salt, $[\alpha]_D^{20}$ −7.4° (c 0.5; water), MS: m/z 1562.0 (reconstructed M).

Example 2

A. A suspension of 4.03 g of E-stilbene-4,4'-dicarboxylic acid in 37.5 ml of acetonitrile and 37.5 ml of tetrahydrofuran was treated at −10° C. with 4.6 ml of triethylamine and 4.3 ml of isobutyl chloroformate and stirred under argon at −4°–0° C. for 50 minutes. A solution of 6.79 g of D-glucamine in 20 ml of water and 10 ml of acetonitrile was added dropwise. After 3 hours at room temperature and 16 hours at 50° C. the mixture was evaporated and the residue was acetylated with acetic anhydride in pyridine. Working-up, separation and deacetylation as described in 1.A. gave (E)-stilbene-4,4'-dicarboxylic acid bis-D-glucit-1-ylamide, $[\alpha]_D^{20}$ −2.6° (c 0.5; dimethyl sulfoxide), MS: m/z 595.4 ([M+H]$^+$).

B. A suspension of 0.59 g of (E)-stilbene-4,4'-dicarboxylic acid bis-D-glucit-1-ylamide and 2.78 g of sulfur trioxide trimethylamine complex in 20 ml of absolute dimethylformamide was stirred at 70°–75° C. for 22 hours. After cooling the upper phase was decanted off. The residue was treated with 1.64 g of sodium acetate in 20 ml of water and evaporated. The residue was taken up in water, again evaporated and purified in distilled water by gel filtration (Sephadex® LH 20). The product fractions were lyophilized and gave (E)-stilbene-4,4'-dicarboxylic acid bis-(2,3,4,5,6-penta-O-sulfo-D-glucit-1-ylamide) decasodium salt, $[\alpha]_D^{20}$ −5.6° (c 0.5; water), MS: m/z 1614.5 (reconstructed M).

Example 3

A. A suspension of 1.34 g of (Z)-stilbene-4,4'-dicarboxylic acid in 12.5 ml of acetonitrile, 12.5 ml of tetrahydrofuran and 12.5 ml of dimethylformamide was treated at −10° C. with 2.0 ml of triethylamine and 1.44 ml of isobutyl chloroformate in 15 ml of tetrahydrofuran and stirred under argon at −15° to −20° C. for 20 minutes. 2.27 g of D-glucamine were then added. After 2 hours at room temperature and 18 hours at 45° C. the mixture was evaporated and the residue was acetylated with acetic anhydride in pyridine. Working-up, separation and deacetylation as described in Example 1.A. gave (Z)-stilbene-4,4'-dicarboxylic acid bis-D-glucit-1-ylamide, $[\alpha]_D^{20}$ −3.8° (c 0.5; dimethyl sulfoxide), MS: m/z 595.4 ([M+H]$^+$).

B. Sulfation of (Z)-stilbene-4,4'-dicarboxylic acid bis-D-glucit-1-ylamide as described under Example 2.B. gave (Z)-stilbene-4,4'-dicarboxylic acid bis-(2,3,4,5,6-penta-O-sulfo-D-glucit-1-ylamide) decasodium salt, $[\alpha]_D^{20}$ −3.5° (c 0.4; water), MS: m/z 1615.5 (reconstructed M).

Example 4

A. A solution of 3.34 g of 4,4'-sulfonyl-bis-(benzoic acid methyl ester) in 100 ml of absolute methanol was treated with 7.24 g of D-glucamine and heated under reflux for 4 days. After cooling the reaction product was filtered off under suction and dried. Acetylation, chromatography and deacetylation analogously to Example 1.A. gave 4,4'-sulfonyl-dibenzoic acid bis-D-glucit-1-ylamide, $[\alpha]_D^{20}$ −7.4° (c 0.5; dimethyl sulfoxide), MS: m/z 633.4 ([M+H]$^+$).

B. Sulfation of 4,4'-sulfonyl-dibenzoic acid bis-D-glucit-1-ylamide as described under Example 1.B. gave 4,4'-sulfonyl-dibenzoic acid bis-(2,3,4,5,6-penta-O-sulfo-D-glucit-1-ylamide) decasodium salt, $[\alpha]_D^{20}$ −3.5° (c 0.4; water), MS: m/z 1652.5 (reconstructed M).

Example 5

A. A solution of 1.472 g of 4,4'-(phenylene-1,4-dioxy)-diphenol in 10 ml of dimethylformamide was slowly added dropwise at 0°–5° C. with the exclusion of moisture to a suspension of 0.48 g of sodium hydride dispersion in 10 ml of dimethylformamide and the mixture was subsequently stirred at room temperature for 1 hour. Thereupon, 2.0 g of ethyl 2-bromopropionate dissolved in 10 ml of dimethylformamide were added dropwise within 5 minutes and the reaction mixture was stirred at 100° C. for 16 hours. Thereafter, the reaction mixture was poured on to 150 ml of ice-water, extracted with methylene chloride, the methylene chloride phase was dried over magnesium sulfate and concentrated.

The resulting oily product was dissolved in a mixture of 50 ml of methanol and 10 ml of 4N potassium hydroxide solution and heated under reflux for 4 hours. After cooling, the majority of the methanol was distilled off under reduced pressure. The residue was then acidified with dilute aqueous hydrochloric acid and the precipitate which thereby formed was filtered off, yielding 2-[4-[4-[4-(1-carboxy-ethoxy)-phenoxy]phenoxy]-phenoxy]-propionic acid, a mixture of the racemic and meso forms, as white crystals with m.p. 135°–136° C.

B. A suspension of 0.877 g of 2-[4-[4-[4-(1-carboxy-ethoxy)-phenoxy]phenoxy]-phenoxy]-propionic acid in 10 ml of acetonitrile was treated with 0.5 ml of 4-methylmorpholine at 0°–5° C. with the exclusion of moisture and the mixture was stirred intensively for 10 minutes. Thereupon, 0.704 g of solid 2-chloro-4,6-dimethoxy-1,3,5-triazine was added and the mixture was stirred at 0°–5° C. for a further 2 hours. Subsequently, 0.725 g of D-glucamine followed by 10 ml of dimethylformamide were added and the mixture was stirred at room temperature for a further 18 hours. Thereupon, the reaction mixture was diluted with water and evaporated several times under reduced pressure at 40°–50° C. The thus-obtained crude product was thereupon chromatographed on LiChroprep RP-18 silica gel with water and subsequently with water containing an increasing amount of methanol. Evaporation of the relevant fractions and drying at 50° C. in a vacuum yielded 2-[4-[4-[4-(1-D-glucit-1-ylcarbamoyl-ethoxy)-phenoxy]-phenoxy]-phenoxy]-propionic acid D-glucit-1-ylamide, a mixture of 3 diastereomers, as a white powder. MS: m/z 765.4 ([M+H]$^+$).

C. The 2-[4-[4-[4-(1-D-glucit-1-ylcarbamoyl-ethoxy)-phenoxy]-phenoxy]-phenoxy]-propionic acid D-glucit-1-ylamide obtained above was converted analogously to Example 1.B. into 2-[4-[4-[4-[1-( 2,3,4,5,6-penta-O-sulfo-D-glucit-1-ylcarbamoyl)-ethoxy]-phenoxy]-phenoxy]-phenoxy]-propionic acid 2,3,4,5,6-penta-O-sulfo-D-glucit-1-ylamide decasodium salt (mixture of 3 diastereomers), $[a]_D^{20}$ −5.7° (c=0.6; water), MS: m/z 1785.5 (reconstructed M).

Example 6

A. A suspension of 0.660 g of 8,8'-diapo-φ,φ-carotene-8,8'-dicarboxylic acid in 10 ml of acetonitrile was treated with 0.5 ml of 4-methylmorpholine at 0°–5° C. with the exclusion of moisture and the mixture was stirred intensively for 10 minutes. Thereupon, 0.705 g of solid 2-chloro-4,6-dimethoxy-1,3,5-triazine was added. The mixture was stirred at 0°–5° C. for a further 2 hours. Subsequently, 0.73 g of D-glucamine followed by 10 ml of dimethylformamide were added and the mixture was stirred at room temperature for a further 18 hours. Thereupon, the reaction mixture was diluted with water and evaporated several times under reduced pressure at 40°–50° C. The mixture was then treated with 40 ml of water and 3 ml of triethylamine, boiled briefly and filtered over a 0.8μ cellulose filter. The filter residue was washed with water and dried at 60° C. in a vacuum and yielded (2E,4E,6E,8E,10E,12E,14E)-2,6,11,15-tetramethyl-hexadeca-2,4,6,8,10,12,14-heptaenedicarboxylic acid bis-D-glucit-1-ylamide as a white powder, MS: m/z 655.6 ([M+H]$^+$).

B. The (2E,4E,6E,8E,10E,12E,14E)-2,6,11,15-tetramethyl-hexadeca-2,4,6,8,10,12,14-heptaenedicarboxylic acid bis-D-glucit-1-ylamide obtained above was converted analogously to Example 1.B. into (2E,4E,6E,8E,10E,12E,14E)-2,6,11,15-tetramethyl-hexadeca- 2,4,6,8,10,12,14-heptaenedicarboxylic acid bis-(2,3,4,5,6-penta-O-sulfo-D-glucit-1-ylamide) decasodium salt, $[\alpha]_D^{20}$ −4.3° (c 1.0; water).

Example 7

A. 24.9 g of 4-nitro-phenyl isocyanate were added portionwise during one hour at 5°–10° C. to a suspension of 27.0 g of D-glucamine in 500 ml of dry dimethylformamide. After stirring at room temperature for 3 hours the mixture was treated with 800 ml of methanol. The resulting precipitate was filtered off under suction, washed with methanol and ether and dried, then suspended in 350 ml of water, filtered off under suction, washed with water and dried. There was obtained 1-D-glucit-1-yl-3-(4-nitro-phenyl)-urea, $[a]_D^{20}$ −17.4° (c 0.5; dimethyl sulfoxide), MS: m/z 346.2 ([M+H]$^+$).

B. A solution of 18 g of 1-D-glucit-1-yl-3-(4-nitro-phenyl)-urea in 250 ml of pyridine was treated with 125 ml of acetic anhydride, stirred at room temperature for 6 hours and concentrated under reduced pressure. The residue was taken up in ethyl acetate and washed with ice-water, 2N aqueous sulfuric acid, water, saturated aqueous sodium hydrogen carbonate solution and saturated sodium chloride solution, dried over magnesium sulfate and evaporated. This crude product was dissolved in 300 ml of ethanol and 160 ml of 1N hydrochloric acid and hydrogenated over 2.9 g of 10% palladium on active charcoal at room temperature and 1.1 bar. After 4 hours the reaction mixture was suction filtered over a filter aid and washed with ethanol/water. The filtrate was concentrated, taken up in ethyl acetate and washed with saturated hydrogen carbonate solution and saturated sodium chloride solution. The organic phase was dried over magnesium sulfate and concentrated. The residue was chromatographed over silica gel and product fractions were crystallized from methylene chloride/ether/hexane. There resulted 1-(4-amino-phenyl)-3-(2,3,4,5,6-penta-O-acetyl-D-glucit-1-yl)-urea, $[a]_D^{20}$ +13.8° (c 0.5; chloroform), MS: m/z 526.3 ([M+H]$^+$).

C. A solution of 2.1 g of 1-(4-aminophenyl)-3-(2,3,4,5,6-penta-O-acetyl-D-glucit-1-yl)-urea in 10 ml of tetrahydrofuran was treated at 5°–10° C. with 1.6 ml of 4-methylmorpholine and 410 mg of isophthaloyl dichloride. After stirring at room temperature for 3 hours the mixture was poured onto ice-water and extracted with ethyl acetate. The organic phases were washed with saturated sodium chloride solution and water, dried over magnesium sulfate and concentrated. The residue was chromatographed on silica gel. Product fractions were evaporated and deacetylated as described under Example 1.A. There resulted N,N'-bis-[4-[3-(D-glucit-1-yl)-ureido]-phenyl]-isophthalamide, $[a]_D^{20}$ −10.0° (c 0.2; dimethyl sulfoxide), MS: m/z 760.5 ($M^+$).

D. Sulfation of N,N'-bis-[4-[3-(D-glucit-1-yl)-ureido]-phenyl]-isophthalamide as described under Example 2.B. gave N,N'-bis-[4-[3-(2,3,4,5,6-penta-O-sulfo-D-glucit-1-yl)-ureido]-phenyl]-isophthalamide decasodium salt, $[\alpha]_D^{20}$ +1.2° (c 0.5; water), MS: m/z 1781.0 (reconstructed M).

Example 8

A. A solution of 1.74 g of toluene-2,4-diyl diisocyanate in 50 ml of dimethylformamide was treated with 3.8 g of D-glucamine at 0° C. and stirred at room temperature for 5 hours. The solvent was evaporated in a high vacuum. The residue was treated with 100 ml of methanol, stirred for 30 minutes and filtered off under suction. The suction filter material was washed with methanol and ether, dried and gave 3,3'-di-D-glucit- 1-yl-1,1'-(toluene-2,4-diyl)-diurea, $[a]_D^{20}$ −12.4° (c 0.5; dimethyl sulfoxide), MS: m/z 537.3 ($M^+$).

B. Sulfation of 3,3'-di-D-glucit-1-yl-1,1'-(toluene-2,4-diyl)-diurea as described under Example 2.B. gave 3,3'-bis-(2,3,4,5,6-penta-O-sulfo-D-glucit- 1-yl)-1,1'-(toluene-2,4-diyl)-diurea decasodium salt, $[a]_D^{20}$ −1.4° (c 0.5; water), MS: m/z 1556.5 (reconstructed M).

Example 9

A. A solution of 0.96 g of 1,4-phenylene diisothiocyanate in 30 ml of dimethylformamide was treated with 1.9 g of D-glucamine at 0° C. and stirred at room temperature for 3 hours. The solvent was evaporated in a high vacuum. The residue was treated with 50 ml of methanol, stirred until a uniform suspension was obtained and suction filtered. The suction filter material was washed with methanol and ether, dried and gave 3,3'-di-D-glucit-1-yl-1,1'-(benzene-1,4-diyl)-dithiourea, $[\alpha]_D^{20}$ −17.8° (c 0.5; dimethyl sulfoxide), MS: m/z 555.3 ($M^+$).

B. Sulfation of 3,3'-di-D-glucit-1-yl-1,1'-(benzene-1,4-diyl)-dithiourea as described under Example 2.B. gave 3,3'-bis-(2,3,4,5,6-penta-O-sulfo-D-glucit- 1-yl)-1,1'-(benzene-1,4-diyl)-dithiourea decasodium salt, $[\alpha]_D^{20}$ +4.2° (c 0.5; water), MS: m/z 1574.5 (reconstructed M).

Example 10

A solution of 0.2 g of (E)-stilbene-4,4'-dicarboxylic acid bis-(2,3,4,5,6-penta-O-sulfo-D-glucit-1-ylamide) decasodium salt (see Example 2) in 15 ml of water was hydrogenated at room temperature for 3 hours in the presence of 10% palladium on charcoal. The catalyst was filtered off and the filtrate was concentrated. The residue was purified over an ion exchange column and gave 4,4'-ethylene-dibenzoic acid bis-(2,3,4,5,6-penta-O-sulfo-D-glucit-1-ylamide) decasodium salt, $[\alpha]_D^{20}$ −4.8° (c 0.4; water), MS: m/z 1616.5 (reconstructed M).

Example 11

A. A solution of 14.5 g of D-glucamine in 120 ml of water was covered with a solution of 11.4 g of naphthalene-1,5-disulfonyl chloride in 300 ml of ethyl acetate. 80 ml of a 1.0N sodium hydroxide solution were added dropwise to the vigorously stirred mixture during 4 hours. After stirring at room temperature for 20 hours the aqueous phase was separated, washed once with 100 ml of ethyl acetate and concentrated at 50° C. on a rotary evaporator. The viscous residue was evaporated azeotropically three times with 50 ml of toluene each time, subsequently taken up in a solution of 300 ml of pyridine and 100 ml of acetic anhydride and heated to reflux for 8 hours. The reaction mixture was again concentrated to dryness and partitioned between water and ethyl acetate. The organic phase was washed with water and sodium hydrogen carbonate solution, dried over magnesium sulfate and evaporated. The residue was chromatographed on silica gel in hexane/ethyl acetate as the eluent. 5.6 g of the purified product were dissolved in 100 ml of methanol and treated with 2 mg of sodium. After stirring for 16 hours. the insoluble precipitate was filtered off. This was dried at 50° C. in a high vacuum and gave naphthalene-1,5-disulfonic acid bis-D-glucit-1-ylamide, MS: m/z 615 ($[M+H]^+$); 637 ($[M+Na]^+$).

B. A solution of 2.78 g of naphthalene-1,5-disulfonic acid bis-D-glucit-1-ylamide and 8.8 g of sulfur trioxide trimethylamine complex in 75 ml of absolute dimethylformamide was stirred at 80° C. for 48 hours. The reaction solution was evaporated at 50°–60° C. and the residue was dissolved in a small amount of water. 6.5 g of sodium acetate were added and subsequently the mixture was again evaporated to dryness. Evaporation of in each case 5 ml of water was repeated three times. Gel filtration of the crude product, dissolved in water, on Sephadex® SP 25 and Sephadex® LH 20 yielded naphthalene-1,5-disulfonic acid bis-(2,3,4,5,6-penta-O-sulfo-D-glucit-1-ylamide) decasodium salt, MS: m/z 1635 (reconstructed M).

Example 12

A. A solution of 8.94 ml of diethyl azodicarboxylate in 50 ml of tetrahydrofuran was added dropwise at a maximum 10° C. under argon and while stirring to 11.6 g of 2,3:4,5-di-O-isopropylidene-D-arabinitol, 7.23 g of 4-nitrophenol and 16.4 g of triphenylphosphine in 450 ml of absolute tetrahydrofuran. The mixture was stirred at room temperature for 18 hours. After distilling off the solvent in a water-jet vacuum the residue was chromatographed on silica gel with hexane/methylene choride. There was thus obtained 2,3:4,5-di-O-isopropylidene- 1-O-(4-nitrophenyl)-D-arabinitol, which was recrystallized from hexane. M.p.: 63°–65° C.

B. 9.29 g of 2,3:4,5-di-O-isopropylidene-1-O-(4-nitrophenyl)-D-arabinitol were reduced by catalytic hydrogenation using 2.1 g of Pd-charcoal (10%) in methanol. Filtering off the catalyst and distilling off the solvent in a water-jet vacuum yielded 1-O-(4-amino-phenyl)-2,3:4,5-di-O-isopropylidene-D-arabinitol, MS: m/z 323 ($M^+$).

C. 1.36 g of 1-O-(4-amino-phenyl)-2,3:4,5-di-O-isopropylidene-D-arabinitol in 30 ml of methylene chloride were reacted with 0.42 g of isophthaloyl dichloride with the addition of 1.35 ml of triethylamine at 5° C. under argon; the mixture was stirred at room temperature for 60 hours. After distilling off the solvent in a water-jet vacuum the crude product was recrystallized from methylene chloride/hexane. There was obtained N,N'-bis-[4-(2,3:4,5-di-O-isopropylidene-D-arabinit-1-yloxy)-phenyl]-isophthalamide, MS: m/z 777.4 ($[M+H]^+$).

D. 1.30 g of N,N'-bis-[4-(2,3:4,5-di-O-isopropylidene-D-arabinit-1-yloxy)-phenyl]-isophthalamide in 20 ml of dioxane were stirred under reflux for 3 hours after addition of 1.4 ml of trifluoroacetic acid and of 2.8 ml of distilled water, 2×50 ml of toluene were added and the mixture was concentrated each time in a water-jet vacuum. The resulting residue was dried for 4 hours in a high vacuum at room temperature over phosphorus pentoxide yielding N,N'-bis-(4-D-arabinit-1-yloxy-phenyl)-isophthalamide which was used directly in the next step.

E. 0.7 g of N,N'-bis-(4-D-arabinit-1-yloxy-phenyl)-isophthalamide was reacted with sulfur trioxide trimethylamine complex in analogy to Example 1.B, and yielded N,N'-bis-[4-(2,3,4,5-tetra-O-sulfo-D-arabinit-1-yloxy)-phenyl]-isophthalamide octasodium salt, MS: m/z 1433.0 (reconstructed M).

Example 13

A. Reaction of terephthalic acid and D-glucamine as described under Example 1.A. gave N,N'-bis-D-glucit-1-yl-terephthalamide, $[a]_D^{20}$ −10.0° (c 0.5; dimethyl sulfoxide), MS: m/z 491.7 ([M−H]−).

B. Sulfation of N,N'-bis-D-glucit-1-yl-terephthalamide as described under Example 1.B. gave N,N'-bis-(2,3,4,5,6-penta-O-sulfo-D-glucit-1-yl)-terephthalamide decasodium salt, $[\alpha]_D^{20}$ −9.0° (c 0.5; water).

Example 14

A. Reaction of isophthalic acid and D-glucamine as described under Example 1.A. gave N,N'-bis-D-glucit-1-yl-isophthalamide, $[a]_D^{20}$ −12.5° (c 0,4; dimethyl sulfoxide), MS: m/z 493.4 ([M+H]+).

B. Sulfation of N,N'-bis-D-glucit-1-yl-isophthalamide as described under Example 2.B. gave N,N'-bis-(2,3,4,5,6-penta-O-sulfo-D-glucit-1-yl)-isophthalamide decasodium salt, $[\alpha]_D^{20}$ −9.5° (c 0.4; water), MS: m/z 1512.5 (reconstructed M).

Example 15

A. Reaction of benzophenone-4,4'-dicarboxylic acid and D-glucamine as described under Example 1.A. gave 4,4'-carbonyl-dibenzoic acid bis-D-glucit-1-ylamide, $[\alpha]_D^{20}$ −7.0° (c 0.5; dimethyl sulfoxide), MS: m/z 597.4 ([M+H]+).

B. Sulfation of 4,4'-carbonyl-dibenzoic acid bis-D-glucit-1-ylamide as described under Example 1.B. gave 4,4'-carbonyl-dibenzoic acid bis-(2,3,4,5,6-penta-O-sulfo-D-glucit-1-ylamide) decasodium salt, $[\alpha]_D^{20}$ −7.8° (c 0.5; water).

Example 16

A. Reaction of diphenylmethane-4,4'-dicarboxylic acid and D-glucamine as described under Example 1.A. gave 4,4'-methylene-dibenzoic acid bis-D-glucit-1-ylamide, $[a]_D^{20}$ −6.4° (c 0.5; dimethyl sulfoxide), MS: m/z 583.4 ([M+H]+).

B. Sulfation of 4,4'-methylene-dibenzoic acid bis-D-glucit-1-ylamide as described under Example 1.B. gave 4,4'-methylene-dibenzoic acid bis-(2,3,4,5,6-penta-O-sulfo-D-glucit-1-ylamide) decasodium salt, $[\alpha]_D^{20}$ −6.2° (c 0.5; water), MS: m/z 1602.5 (reconstructed M).

Example 17

A. Reaction of 4,4'-oxy-dibenzoic acid and D-glucamine as described under Example 1.A. gave 4,4'-oxy-dibenzoic acid bis-D-glucit-1-ylamide, $[\alpha]_D^{20}$ −5.8° (c 0.5; dimethyl sulfoxide), MS: m/z 585.2 ([M+H]+).

B. Sulfation of 4,4'-oxy-dibenzoic acid bis-D-glucit-1-ylamide as described under Example 2.B. gave 4,4'-oxy-dibenzoic acid bis-(2,3,4,5,6-penta-O-sulfo-D-glucit-1-ylamide) decasodium salt, $[\alpha]_D^{20}$ −5.2° (c 0.5; water), MS: m/z 1604.5 (reconstructed M).

Example 18

A. Reaction of 4,4'-(hexafluoro-propane-2,2-diyl)-dibenzoic acid and D-glucamine as described under Example 1.A. gave 4,4'-(hexafluoro-propane- 2,2-diyl)-dibenzoic acid bis-D-glucit-1-ylamide, $[\alpha]_D^{20}$ −5.6° (c 0.5; dimethyl sulfoxide), MS: m/z 719.4 ([M+H]+).

B. Sulfation of 4,4'-(hexafluoro-propane-2,2-diyl)-dibenzoic acid bis-D-glucit-1-ylamide as described under Example 1.B. gave 4,4'-(hexafluoro-propane-2,2-diyl)-dibenzoic acid bis-(2,3,4,5,6-penta-O-sulfo-D-glucit-1-ylamide) decasodium salt, $[\alpha]_D^{20}$ −4.6° (c 0.5; water), MS: m/z 1738.5 (reconstructed M).

Example 19

A. Reaction of biphenyl-4,4'-dicarboxylic acid and D-glucamine as described under Example 1.A. gave biphenyl-4,4'-dicarboxylic acid bis-D-glucit-1-ylamide, $[\alpha]_D^{20}$ −4.6° (c 0.2; dimethyl sulfoxide), MS: m/z 569.2 ([M+H]+).

B. Sulfation of biphenyl-4,4'-dicarboxylic acid bis-D-glucit-1-ylamide as described under Example 2.B. gave biphenyl-4,4'-dicarboxylic acid bis-(2,3,4,5,6-penta-O-sulfo-D-glucit-1-ylamide) decasodium salt, $[\alpha]_D^{20}$ −6.4° (c 0.5; water), MS: m/z 1588.5 (reconstructed M).

Example 20

A. Reaction of naphthalene-1,4-dicarboxylic acid and D-glucamine as described under Example 1.A. gave naphthalene-1,4-dicarboxylic acid bis-D-glucit-1-ylamide, $[\alpha]_D^{20}$ −8.6° (c 0.5; dimethyl sulfoxide), MS: m/z 963.4 ([M+H]+).

B. Sulfation of naphthalene-1,4-dicarboxylic acid bis-D-glucit-1-ylamide as described under Example 2.B. gave naphthalene-1,4-dicarboxylic acid bis-(2,3,4,5,6-penta-O-sulfo-D-glucit-1-ylamide) decasodium salt, $[\alpha]_D^{20}$ −14.6° (c 0.5; water), MS: m/z 1562.5 (reconstructed M).

Example 21

A. Reaction of (4-carboxy-phenoxy)-acetic acid and D-glucamine as described under Example 1.A. gave N-D-glucit-1-yl-4-(D-glucit-1-ylcarbamoylmethoxy)-benzamide, $[\alpha]_D^{20}$ −10.8° (c 0.5; dimethyl sulfoxide), MS: m/z 523.4 ([M+H]+).

B. Sulfation of N-D-glucit-1-yl-4-(D-glucit-1-ylcarbamoylmethoxy)-benzamide as described under Example 2.B. gave N-(2,3,4,5,6-penta-O-sulfo-D-glucit- 1-yl)-4-(2,3,4,5,6-penta-O-sulfo-D-glucit-1-ylcarbamoylmethoxy)-benzamide decasodium salt, $[\alpha]_D^{20}$ −14.6° (c 0.5; water), MS: m/z 1562.5 (reconstructed M).

Example 22

A. Reaction of 9-oxo-9H-fluorene-2,7-dicarboxylic acid and D-glucamine as described under Example 3.A. gave 9-oxo-9H-fluorene-2,7-dicarboxylic acid bis-D-glucit-1-ylamide, $[\alpha]_D^{20}$ −2.5° (c 0.2; dimethyl sulfoxide), MS: m/z 595.4 ([M+H]+).

B. Sulfation of 9-oxo-9H-fluorene-2,7-dicarboxylic acid bis-D-glucit-1-ylamide as described under Example 2.B. gave 9-oxo-9H-fluorene-2,7-dicarboxylic acid bis-(2,3,4,5,6-penta-O-sulfo-D-glucit-1-ylamide) decasodium salt, $[\alpha]_D^{20}$ –7.4° (c 0.5; water), MS: m/z 1614.5 (reconstructed M).

Example 23

A. Reaction of 1,1';4',1''-terphenyl-4,4''-dicarboxylic acid and D-glucamine as described under Example 3.A. gave 1,1';4',1''-terphenyl-4,4''-dicarboxylic acid bis-D-glucit-1-ylamide, MS: m/z 645.6 ([M+H]$^+$).

B. Sulfation of 1,1';4',1''g-terphenyl-4,4''-dicarboxylic acid bis-D-glucit-1-ylamide as described under Example 2.B. gave 1,1';4',1''-terphenyl-4,4''-dicarboxylic acid bis-(2,3,4,5,6-penta-O-sulfo-D-glucit-1-ylamide) decasodium salt. $[\alpha]_D^{20}$ –5.6° (c 0.5; water), MS: m/z 1665.0 (reconstructed M).

Example 24

A. Analogously to Example 6.A., from (2E,4E,6E)-2,7-dimethyl-octa-2,4,6-trienedicarboxylic acid and D-glucamine there was obtained (2E,4E,6E)-2,7-dimethyl-octa-2,4,6-trienedicarboxylic acid bis-D-glucit-1-ylamide as a white powder, MS: m/z 523.4 ([M+H]$^+$).

B. The (2E,4E,6E)-2,7-dimethyl-octa-2,4,6-trienedicarboxylic acid bis-D-glucit-1-ylamide obtained above was converted into (2E,4E,6E)-2,7-dimethyl-octa-2,4,6-trienedicarboxylic acid bis-(2,3,4,5,6-penta-O-sulfo-D-glucit-1-ylamide) decasodium salt, $[\alpha]_D^{20}$ –6.3° (c 0.7; water), analogously to Example 1.B.

Example 25

A. 1.51 g of 4-(aminomethyl)-benzoic acid and 2.76 g of potassium carbonate were dissolved in 40 ml of water by heating. Thereupon, 1.72 g of 4,4'-sulfonyl-dibenzoyl chloride suspended in 40 ml of toluene were added. The reaction mixture was stirred intensively at room temperature for 18 hours and subsequently evaporated to dryness under reduced pressure, boiled up in water and filtered through a 0.8 m cellulose filter. The filter residue was thereupon again boiled up in dilute hydrochloric acid and once more filtered over a 0.8 m cellulose filter, yielding 4,4'-sulfonyl-dibenzoic acid bis-(4-carboxy-benzylamide) as colourless crystals, MS: m/z 571.3 ([M–H]$^-$).

B. Analogously to Example 6.A., from 4,4'-sulfonyl-dibenzoic acid bis-(4-carboxy-benzylamide) and D-glucamine there was obtained 4,4'-sulfonyl-dibenzoic acid bis-(4-D-glucit-1-ylcarbamoyl-benzylamide) as a white powder, $[\alpha]_D^{20}$ –4.0° (c 0.4; dimethyl sulfoxide), MS: m/z 899.4 ([M+H]$^+$).

C. The 4,4'-sulfonyl-dibenzoic acid bis-(4-D-glucit-1-ylcarbamoyl-benzylamide) obtained above was converted analogously to Example 1.B. into 4,4'-sulfonyl-dibenzoic acid bis-[4-(2,3,4,5,6-penta-O-sulfo-D-glucit- 1-ylcarbamoyl)-benzylamide] decasodium salt $[\alpha]_D^{20}$ –3.6° (c 0.5; water), MS: m/z 1920.0 (reconstructed M).

Example 26

A. Reaction of toluene-2,6-diyl diisocyanate and D-glucamine as described under Example 8.A. gave 3,3'-di-D-glucit-1-yl-1,1'-(toluene-2,6-diyl)-diurea, $[\alpha]_D^{20}$ –8.4° (c 0.5; dimethyl sulfoxide), MS: m/z 537.5 ([M+H]$^+$).

B. Sulfation of 3,3'-di-D-glucit-1-yl-1,1'-(toluene-2,6-diyl)-diurea as described under Example 2.B. gave 3,3'-bis-(2,3,4,5,6-penta-O-sulfo-D-glucit- 1-yl)-1,1'-(toluene-2,6-diyl)-diurea decasodium salt, $[\alpha]_D^{20}$ –1.6° (c 0.5; water), MS: m/z 1556.5 (reconstructed M).

Example 27

A. Reaction of (benzene-1,3-diyl-dimethylene)diisocyanate and D-glucamine as described under Example 8.A. gave 3,3'-di-D-glucit-1-yl-1,1'-(benzene-1,3-diyl-dimethylene)-diurea, $[\alpha]_D^{20}$ –4.0° (c 0.5; dimethyl sulfoxide), MS: m/z 551.6 ([M+H]$^+$).

B. Sulfation of 3,3'-di-D-glucit-1-yl-1,1'-(benzene-1,3-diyl-dimethylene)-diurea as described under Example 2.B. gave 3,3'-bis-(2,3,4,5,6-penta-O-sulfo-D-glucit-1-yl)-1,1'-(benzene-1,3-diyl-dimethylene)-diurea decasodium salt, $[\alpha]_D^{20}$ –1.6° (c 0.5; water), MS: m/z 1556.5 (reconstructed M).

Example 28

A. Reaction of 2,2'-dichloro-4,4'-methylene-bis-phenyl isocyanate and D-glucamine as described under Example 8.A. gave 3,3'-D-glucit-1-yl- 1,1'-(3,3'-dichloro-4,4'-methylene-diphenyl)-diurea, $[\alpha]_D^{20}$ –7.5° (c 0.5; dimethyl sulfoxide), MS: m/z 681.4 ([M+H]$^+$).

B. Sulfation of 3,3'-D-glucit-1-yl-1,1'-(3,3'-dichloro-4,4'-methylene-diphenyl)-diurea as described under Example 2.B. gave 3,3'-bis( 2,3,4,5,6-penta-O-sulfo-D-glucit-1-yl)-1,1'-(3,3'-dichloro-4,4'-methylene-diphenyl)-diurea decasodium salt, $[\alpha]_D^{20}$ +0.8° (c 0.5; water), MS: m/z 1702.0 (reconstructed M).

Example 29

A. Reaction of 4,4'-(3,3'-dimethyl-biphenyl-diyl)diisocyanate and D-glucamine as described under Example 8.A. gave 3,3'-D-glucit-1-yl-1,1'-(3,3'-dimethyl-biphenyl-4,4'-diyl)-diurea, $[\alpha]_D^{20}$ –15.5° (c 0.2; dimethyl sulfoxide), MS: m/z 627.3 ([M+H]$^+$).

B. Sulfation of 3,3'-D-glucit-1-yl-1,1'-(3,3'-dimethyl-biphenyl-4,4'-diyl)-diurea as described under Example 2.B. gave 3,3'-bis-(2,3,4,5,6-penta-O-sulfo-D-glucit- 1-yl)-1,1'-(3,3'-dimethyl-biphenyl-4,4'-diyl)-diurea decasodium salt, $[a]_D^{20}$ +1.0° (c 0.5 water), MS: m/z 1647.0 (reconstructed M).

Example 30

A. Reaction of (3,3'-dimethoxy-biphenyl-4,4'-diyl)diisocyanate and D-glucamine as described under Example 8.A. gave 3,3'-D-glucit-1-yl-1,1'-(3,3'-dimethoxy-biphenyl-4,4'-diyl)-diurea, $[a]_D^{20}$ –10.0° (c 0.2; dimethyl sulfoxide), MS: m/z 659.3 ([M+H]$^+$).

B. Sulfation of 3,3'-D-glucit-1-yl-1,1'-(3,3'-dimethoxy-biphenyl-4,4'-diyl)-diurea as described under Example 2.B. gave 3,3'-bis-(2,3,4,5,6-penta-O-sulfo-D-glucit- 1-yl)-1,1'-(3,3'-dimethoxy-biphenyl-4,4'-diyl)-diurea decasodium salt, $[\alpha]_D^{20}$ 1.6° (c 0.5 water).

Example 31

A. Reaction of 4,4'-(3,3'-dichloro-biphenyl-diyl)diisocyanate and D-glucamine as described under Example 8.A. gave 3,3'-D-glucit-1-yl-1,1'-(3,3'-dichloro-biphenyl-4,4'-diyl)-diurea, MS: m/z 667.4 ([M+H]$^+$).

B. Sulfation of 3,3'-D-glucit-1-yl-1,1'-(3,3'-dichloro-biphenyl-4,4'-diyl)-diurea as described under Example 2.B. gave 3,3'-bis-(2,3,4,5,6-penta-O-sulfo-D-glucit- 1-yl)-1,1'-(3,3'-dichloro-biphenyl-4,4'-diyl)diurea decasodium salt, $[\alpha]_D^{20}$ +4.6° (c 0.5; water).

Example 32

A. Reaction of 4,4'-diphenylmethane diisocyanate and D-glucamine as described under Example 8.A. gave 3,3'-di-D-glucit-1-yl-1,1'-(4,4'-methylene-diphenyl)-diurea, $[\alpha]_D^{20}$ −13.2° (c 0.2; dimethyl sulfoxide), MS: m/z 613.4 ([M+H]$^+$).

B. Sulfation of 3,3'-di-D-glucit-1-yl-1,1'-(4,4'-methylene-diphenyl)-diurea as described under Example 2.B. gave 1,1'-(4,4'-methylene-diphenyl)- 3,3'-bis-(2,3,4,5,6-penta-O-sulfo-D-glucit-1-yl)-diurea decasodium salt, $[\alpha]_D^{20}$ −0.8° (c 0.5; water).

Example 33

A. Reaction of 1-(4-aminophenyl)-3-(2,3,4,5-penta-O-acetyl-D-glucit-1-yl)-urea and terephthaloyl dichloride as described under Example 7.C. gave N,N'-bis-[4-[3-(D-glucit-1-yl)-ureido]-phenyl]-terephthalamide.

B. Sulfation of N,N'-bis-[4-[3-(D-glucit-1-yl)-ureido]-phenyl]-terephthalamide as described under Example 2.B. gave N,N'-bis-[4-[3-(2,3,4,5,6-penta-O-sulfo-D-glucit-1-yl)-ureido]-phenyl]-terephthalamide decasodium salt, $[\alpha]_D^{20}$ 0.0° (c 0.2; water), MS: m/z 1781.0 (reconstructed M).

Example 34

A. Reaction of 1-(4-aminophenyl)-3-(2,3,4,5,6-penta-O-acetyl-D-glucit-1-yl)-urea and fumaric acid dichloride as described under Example 7.C. gave N,N'-bis-[4-[3-(D-glucit-1-yl)-ureido]-phenyl]-fumaramide, $[\alpha]_D^{20}$ −12.5° (c 0.2; dimethyl sulfoxide), MS: m/z 711.4 ([M+H]$^+$).

B. Sulfation of N,N'-bis-[4-[3-(D-glucit-1-yl)-ureido]-phenyl]-fumaramide as described under Example 2.B. gave N,N'-bis-[4-[3-( 2,3,4,5,6-penta-O-sulfo-D-glucit-1-yl)-ureido]-phenyl]-fumaramide decasodium salt, $[\alpha]_D^{20}$ +1.0° (c 0.5; water), MS: m/z 1731.0 (reconstructed M).

Example 35

A. Reaction of 4,4'-diisothiocyanato-E-stilbene-2,2'-disulfonic acid disodium salt and D-glucamine as described under Example 9.A. gave (E)-4,4'-bis-(3-D-glucit-1-yl-thioureido)-stilbene-2,2'-disulfonic acid disodium salt, $[\alpha]_D^{20}$ −16.4° (c 0.2; dimethyl sulfoxide), MS: m/z 860.0 (M$^+$).

B. Sulfation of (E)-4,4'-bis-(3-D-glucit-1-yl-thioureido)-stilbene-2,2'-disulfonic acid as described under Example 2.B. gave (E)-4,4'-bis-[3-(2,3,4,5,6-penta-O-sulfo-D-glucit-1-yl)-thioureido]-stilbene-2,2'-disulfonic acid dodecasodium salt, $[\alpha]_D^{20}$ +2.0° (c 0.5; water), MS: m/z 1880.5 (reconstructed M).

Example 36

A. 1 g of terephthaloyl dichloride suspended in 15 ml of toluene was added to a solution of 1.92 g of N-methyl-D-glucamine and 1.36 g of potassium carbonate in 15 ml of water. The reaction mixture was stirred intensively at room temperature for 20 hours, subsequently concentrated under reduced pressure and then chromatographed on LiChroprep RP-18 silica gel with water and subsequently with water containing an increasing amount of methanol. Concentration of the relevant fractions and drying in a vacuum gave N,N'-di-D-glucit-1-yl-N,N'-dimethyl-terephthalamide as colourless crystals $[\alpha]_D^{20}$ −7.4° (c 0.5; dimethyl sulfoxide), MS: m/z 521.2 ([M+H]$^+$).

B. The N,N'-di-D-glucit-1-yl-N,N'-dimethyl-terephthalamide obtained above was converted analogously to Example 1.B. into N,N'-dimethyl-N,N'-bis-( 2,3,4,5,6-penta-O-sulfo-D-glucit-1-yl)-terephtalamide decasodium salt, $[\alpha]_D^{20}$ −14.2° (c 0.5; water), MS: m/z 1541.0 (reconstructed M).

Example 37

A. Analogously to Example 5.B., from 9-oxo-9H-fluorene-2,7-dicarboxylic acid and N-methyl-D-glucamine there was obtained 9-oxo-9H-fluorene-2,7-dicarboxylic acid bis-[(D-glucit-1-yl)-methyl-amide] as a yellowish powder, $[\alpha]_D^{20}$ −2° (c 0.4; dimethyl sulfoxide), MS: 623.4 ([M+H]$^+$).

B. The 9-oxo-9H-fluorene-2,7-dicarboxylic acid bis-[(D-glucit-1-yl)-methyl-amide] obtained above was converted analogously to Example 1.B. into 9-oxo-9H-fluorene-2,7-dicarboxylic acid bis-[methyl-(2,3,4,5,6-penta-O-sulfo-D-glucit- 1yl)-amide] decasodium salt, $[\alpha]_D^{20}$ +2.2° (c 0.5; water).

Example 38

A. Reaction of toluene-2,6-diyl diisocyanate and N-methyl-D-glucamine as described under Example 8.A. gave 3,3'-di-D-glucit-1-yl-3,3'-dimethyl 1,1'-(toluene-2,6-diyl)-diurea, $[\alpha]_D^{20}$ +35.5° (c 0.2; dimethyl sulfoxide), MS: m/z 565.4 ([M+H]$^+$).

B. Sulfation of 3,3'-di-D-glucit-1-yl-3,3'-dimethyl-1,1'-(toluene-2,6-diyl)-diurea as described under Example 2.B. gave 3,3'-dimethyl-3,3'-bis-( 2,3,4,5,6-penta-O-sulfo-D-glucit-1-yl)-1,1'-(toluene-2,6-diyl)-diurea decasodium salt, $[\alpha]_D^{20}$ −1.6° (c 0.5; water), MS: m/z 1584.5 (reconstructed M).

Example 39

A. A solution of 7.25 g of D-glucamine in 22 ml of 1.0N sodium hydroxide was treated with a solution of 3.66 g of diphenyl-4,4'-disulfonyl chloride in 100 ml of tetrahydrofuran. After stirring at room temperature for 56 hours the aqueous phase was separated and concentrated at 50° C. on a rotary evaporator. The residue was evaporated azeotropically three times with 50 ml of toluene each time and subsequently acylated with acetic anhydride in pyridine. Working-up and purification were effected as described under 11.A. and yielded biphenyl-4,4'-disulfonic acid bis-D-glucit-1-ylamide, MS: m/z 640 ([M−H]$^−$).

B. Sulfation of biphenyl-4,4'-disulfonic acid bis-D-glucit-1-ylamide as described under Example 11.B. yielded biphenyl-4,4'-disulfonic acid bis-(2,3,4,5,6-penta-O-sulfo-D-glucit-1-ylamide) decasodium salt, MS: m/z 1661 (reconstructed M).

Example 40

A. Reaction of 4,4'-oxy-bis-(benzenesulfonyl chloride) with D-glucamine as described under Example 11.A. gave 4,4'-oxy-dibenzene sulfonic acid bis-D-glucit-1-ylamide, MS: m/z 657 ([M+H]$^+$).

B. Sulfation of 4,4'-oxy-dibenzenesulfonic acid bis-D-glucit-1-ylamide as described under Example 11.B. yielded 4,4'-oxy-dibenzenesulfonic acid bis-(2,3,4,5,6-penta-O-sulfo-D-glucit-1-ylamide) decasodium salt, $[\alpha]_D^{20}$ +4.4° (c 1.0; water).

Example 41

A. 0.68 g of 1-O-(4-amino-phenyl)-2,3:4,5-di-O-isopropylidene-D-arabinitol (example 12.B) were reacted in 15 ml of methylene chloride with 0.21 g of terephthaloyl dichloride with the addition of 0.69 ml of triethylamine at 5° C. under argon; the mixture was stirred at room temperature for 60 hours. After distillation of the solvent in a water-jet vacuum the crude product was chromatographed on silica gel with methylene chloride/methanol. There was obtained N,N'-bis-[4-(2,3:4,5-di-O-isopropylidene-D-arabinit-1-yloxy)-phenyl]-terephthalamide, MS: m/z 778.4 (M+H)$^+$.

B. 0.77 g N,N'-bis-[4-(2,3:4,5-di-O-isopropylidene-D-arabinit-1-yloxy)-phenyl]-terephthalamide in 15 ml of dioxan were stirred at as 50° C. for 18 hours after addition of 1.0 ml of trifluoroacetic acid and 2 ml of distilled H$_2$O; 2×50 ml of toluene were added, the mixture was concentrated in a water-jet vacuum each time and the residue was dried in a high vacuum at 50° C. over phosphorus pentoxide for 3 hours. There was obtained N,N'-bis-(4-D-arabinit-1yloxy-phenyl)-terephthalamide which was used directly in the next step.

C. 0.3 g of N,N'-bis-(4-D-arabinit-1yloxy-phenyl)-terephthalamide were reacted with sulfur trioxide trimethylamine complex in analogy to Example 1.B. There was thus obtained N,N'-bis-[4-(2,3,4,5-tetra-O-sulfo-D-arabinit-1-yloxy)-phenyl]-terephthalamide octasodium salt, MS: m/z 1432.0 (reconstructed M).

Example 42

A. 0.65 g of 1-O-(4-amino-phenyl)-2,3:4,5-di-O-isopropylidene-D-arabinitol and 0.16 g of N,N-carbonyl-diimidazole in 15 ml of tetrahydrofuran were stirred at room temperature under argon for 16 hours. The reaction mixture was evaporated; the residue was treated with ice-water and extracted with ether. The combined ether phases were washed with dil. hydrochloric acid and water, dried over magnesium sulfate, filtered and evaporated. There was obtained 1,3-bis-[4-(2,3:4,5-di-O-isopropylidene-D-arabinit-1-yloxy)-phenyl]-urea which was recrystallized from methylene chloride/n-hexane, MS: m/z 673.4 ([M+H]$^+$).

B. 0.40 g of 1,3-bis-[4-(2,3:4,5-di-O-isopropylidene-D-arabinit-1-yloxy)-phenyl]-urea were stirred under reflux for 4 hours with trifluoroacetic acid (50%) in 15 ml of dioxan in analogy to Example 12.D. and worked-up analogously. There was obtained 1,3-bis-(4-D-arabinit-1-1yloxy-phenyl)-urea which was used directly in the next step.

C. 0.37 g of 1,3-bis-(4-D-arabinit-1-lyloxy-phenyl)-urea were reacted with sulfur trioxide trimethylamine complex in analogy to Example 1.B. There was thus obtained 1,3-bis-[4-(2,3,4,5-tetra-O-sulfo-D-arabinit- 1-yloxy)-phenyl]-urea octasodium salt, MS: m/z 1328.5 (reconstructed M).

Example 43

A. 0.995 g of terphthalic acid monomethyl ester chloride and 0.756 g of methyl 4-(methylamino)-benzoate were dissolved in 25 ml of acetone and treated with 0.691 g of anhydrous potassium carbonate. The reaction mixture was stirred at room temperature for 30 hours and was evaporated. The residue was treated with water and the crystals were filtered off yielding N-(4-methoxycarbonyl-phenyl)-N-methyl-terephthalamic acid methyl ester in the form of colourless crystals, MS: m/z 327 (M$^+$).

B. 0.99 g of N-(4-methoxycarbonylphenyl)-N-methyl-terephthalamic acid methyl ester was dissolved in 10 ml of acetonitrile and treated with 10 ml of 1N sodium hydroxide solution and the reaction mixture was stirred at room temperature for 16 hours. The mixture was then acidified with 1N hydrochloric acid and the resulting precipitate was filtered off yielding N-(4-carboxy-phenyl)-N-methyl-terephthalamic acid, which was used directly in the next step.

C. Analogously to Example 5.B., from N-(4-methoxycarbonylphenyl)-N-methyl-terephthalamic acid and D-glucamine there was obtained N-(D-glucit-1-yl)-N'-(4-D-glucit-1-ylcarbamoyl-phenyl)-N'-methyl-terephthalamide as a white powder, MS: m/z 626.4 ([M+H]$^+$).

D. The N-(D-glucit-1-yl)-N'-(4-D-glucit-1-ylcarbamoyl-phenyl)-N'-methyl-terephthalamide obtained above was converted analogously to Example 1.B. into N'-methyl-N-(2,3,4,5,6-penta-O-sulfo-D-glucit-1-yl)-N'-[4-(2,3,4,5,6-penta-O-sulfo-D-glucit-1-ylcarbamoyl)-phenyl]-terephthalamide decasodium salt $[\alpha]_D^{20}$ −5.7° (c 0.6; water), MS: m/z 1645.5 (reconstructed M).

Example 44

A. Analogously to Example 43.A. and 43.B., from terephthalic acid monomethyl ester chloride and methyl 4-aminobenzoate there was obtained N-(4-carboxy-phenyl)-terephthalamic acid as a colourless powder, MS: m/z 284.1 ([M−H]$^-$).

B. Analogously to Example 6.A., from N-(4-carboxyphenyl)-terephthalamic acid and D-glucamine there was obtained N-D-glucit-1-yl-N'-(4-D-glucit- 1-ylcarbamoyl-phenyl)-terephthalamide as a white powder, MS: m/z 612.4 ([M+H]$^+$).

C. The N-D-glucit-1-yl-N'-(4-D-glucit-1-ylcarbamoyl-phenyl)-terephthalamide obtained above was converted analogously to Example 1.B. into N-(2,3,4,5,6-penta-O-sulfo-D-glucit-1-yl)-N'-[4-(2,3,4,5,6-penta-O-sulfo-D-glucit- 1-ylcarbamoyl)-phenyl]-terephthalamide decasodium salt, $[\alpha]_D^{20}$ −6.1° (c 0.7; water), MS: m/z 1632.0 (reconstructed M).

Example 45

A. (Z)-But-2-enedicarboxylic acid 3-carboxy-4-(4-chloro-phenoxy)-phenylamide was acquired from MAYBRIDGE CHEMICAL COMPANY LTD., Trevillett, Tintagel Cornwall, UK. It is prepared in the following manner:

A.1. Methyl 2-(4-chlorophenoxy)-5-nitro-benzoate is reduced to methyl 5-amino-2-(4-chlorophenoxy)-benzoate using palladium/charcoal as the catalyst with the aid of hydrogen in a solvent such as methanol. Alternatively, this reduction step is carried out using tin tetrachloride in aqueous hydrochloric acid or using sodium sulfide in methanol/water at in each case elevated temperature either with the aforementioned ester or the free 2-(4-chlorophenoxy)-5-nitrobenzoic acid to give 5-amino-2-(4-chlorophenoxy)-benzoic acid, which subsequently is converted into methyl 5-amino-2-(4-chlorophenoxy)-benzoate by heating in methanolic hydrochloric acid.

A.2. Reaction of methyl 5-amino-2-(4-chlorophenoxy)-benzoate with maleic anhydride in a solvent such as methylene chloride or dimethylformamide in the presence of pyridine or 4-dimethylaminopyridine gives (Z)-but-2-enedicarboxylic acid 3-carbomethoxy-4-(4-chloro-phenoxy)-phenylamide which is converted by saponification with aqueous sodium hydroxide or potassium hydroxide in water and a second solvent such as methanol, ethanol or acetonitrile into (Z)-but-2-enedicarboxylic acid 3-carboxy-4-(4-chloro-phenoxy)-phenylamide, melting point: 224°–226° C.

B. Analogously to Example 5.B., from (Z)-but-2-enedicarboxylic acid 3-carboxy-4-(4-chloro-phenoxy)-phenylamide and D-glucamine there was obtained (Z)-but-2-enedicarboxylic acid 1-[4-(4-chloro-phenoxy)-3-D-glucit-1-ylcarbamoyl-phenyl]amide 4-D-glucit-1-ylamide as a white powder, MS: m/z 688.4 ([M+H]$^+$).

C. The (Z)-but-2-enedicarboxylic acid 1-[4-(4-chloro-phenoxy)-3-D-glucit- 1-ylcarbamoyl-phenyl]amide 4-D-glucit-1-ylamide obtained above was converted analogously to Example 1.B. into (Z)-but-2-enedicarboxylic acid 1-[4-(4-chloro-phenoxy)-3-(2,3,4,5,6-penta-O-sulfo-D-glucit-1-ylcarbamoyl)-phenyl]-amide 4-(2,3,4,5,6-penta-O-sulfo-D-glucit-1-yl)-amide decasodium salt, $[\alpha]_D^{20}$ –4° (c 0.5; water), MS: m/z 1708.0 (reconstructed M).

Example 46

A. 3-Carboxy-4-(4-chloro-phenoxy)-succinic acid monoanilide was acquired from MAYBRIDGE CHEMICAL COMPANY LTD., Trevillett, Tintagel Cornwall, UK. It is prepared as described in Example 45.A. by replacing maleic anhydride by succinic anhydride. There is thus obtained N-[3-carboxy-4-(4-chloro-phenoxy)-phenyl]-succinic acid monoamide, melting point: 226°–228° C.

B. Analogously to Example 5.B., from N-[3-carboxy-4-(4-chloro-phenoxy)-phenyl]-succinic acid monoamide and D-glucamine there was obtained N1-[4-(4-chloro-phenoxy)-3-D-glucit-1-ylcarbamoyl-phenyl]-N4-D-glucit-1-yl-succinamide as a white powder, MS: m/z 690.2 ([M+H]$^+$).

C. The N1-[4-(4-chloro-phenoxy)-3-D-glucit-1-ylcarbamoyl-phenyl]-N4-D-glucit-1-yl-succinamide obtained above was converted analogously to Example 1.B. into N1-[4-(4-chloro-phenoxy)-3-(2,3,4,5,6-penta-O-sulfo-D-glucit- 1-ylcarbamoyl)-phenyl]-N4-(2,3,4,5,6-penta-O-sulfo-D-glucit-1-yl)-succinamide decasodium salt, $[\alpha]_D^{20}$ –4.6° (c 0.5; water), MS: m/z 1710.5 (reconstructed M).

Example 47

A. (Z)-But-2-enedicarboxylic acid 3-carboxy-4-(2-methoxyethoxy)-phenylamide was acquired from MAYBRIDGE CHEMICAL COMPANY LTD., Trevillett, Tintagel Cornwall, UK. It is prepared in the following manner:

A.1. Methyl 2-hydroxy-5-nitro-benzoate is converted in the presence of a base such as potassium carbonate, sodium hydride or sodium methylate in a solvent such as methanol or dimethylformamide at an elevated temperature with 1-bromo-2-methoxyethane or 2-methoxyethyl 4-toluenesulfonate into methyl 2-(2-methoxyethoxy)-5-nitro-benzoate. This is subsequently converted as described in Examples 45.A.1. and 45.A.2. into (Z)-but-2-enedicarboxylic acid 3-carboxy- 4-(2-methoxy-ethoxy)-phenylamide, melting point: 202°–205° C.

B. Analogously to Example 5.B., from (Z)-but-2-enedicarboxylic acid 3-carboxy-4-(2-methoxy-ethoxy)-phenylamide and D-glucamine there was obtained (Z)-but-2-enedicarboxylic acid 1-D-glucit-1-ylamide 4-[3-D-glucit-1-ylcarbamoyl-4-(2-methoxy-ethoxy)-phenyl]-amide as a white powder, elementary analysis calculated for $C_{26}H_{41}N_3O_{15} \times 1.1 H_2O$: C=47.65%, H=6.64%, N=6.41%; found: C=47.47%, H=6.65%, N=6.46%.

C. The (Z)-but-2-enedicarboxylic acid 1-D-glucit-1-ylamide 4-[3-D-glucit- 1-ylcarbamoyl-4-(2-methoxy-ethoxy)-phenyl]-amide obtained above was converted analogously to Example 1.B. into (Z)-but-2-enedicarboxylic acid 1-(2,3,4,5,6-penta-O-sulfo-D-glucit-1-yl)-amide 4-[4-(2-methoxy-ethoxy)-3-(2,3,4,5,6-penta-O-sulfo-D-glucit-1-ylcarbamoyl)-phenyl]-amide decasodium salt, $[\alpha]_D^{20}$ –2.7° (c 0.6; water), MS: m/z 1655.5 (reconstructed M).

Example 48

A. A solution of 1.0 g of (Z)-but-2-enedicarboxylic acid 1-D-glucit-1-ylamide 4-[3-D-glucit-1-ylcarbamoyl-4-(2-methoxy-ethoxy)-phenyl]-amide in 8 ml of water was treated with 100 mg of palladium on charcoal catalyst (10%) and hydrogenated in a hydrogen atmosphere for 2 hours. The catalyst was filtered off and the filtrate was lyophilized yielding N1-D-glucit-1-yl-N4-[3-D-glucit-1-ylcarbamoyl-4-(2-methoxy-ethoxy)-phenyl]-succinamide as a greyish powder, MS: m/z 638.4 ([M+H]$^+$).

B. The N1-D-glucit-1-yl-N4-[3-D-glucit-1-ylcarbamoyl-4-(2-methoxy-ethoxy)-phenyl]-succinamide obtained above was converted analogously to Example 1.B. into N1-[4-(2-methoxy-ethoxy)-3-(2,3,4,5,6-penta-O-sulfo-D-glucit-1-ylcarbamoyl)-phenyl]-N4-(2,3,4,5,6-penta-O-sulfo-D-glucit-1-yl)-succinamide decasodium salt, $[\alpha]_D^{20}$ –2.4° (c 0.5; water), MS: m/z 1657.5 (reconstructed M).

Example 49

A. 1.07 g of 4-(4-hydroxy-phenyl)-benzoic acid, 2.8 g of anhydrous potassium carbonate, 0.65 g of bis(4-fluorophenyl) sulfone and 70 mg of dicyclohexano-18-crown-6 were suspended in 18 ml of 1,3-dimethyl-2-imidazolidinone and stirred under argon at 150° C. for 6 hours and at 175° C. for a further 3 hours. Thereupon, the reaction mixture was poured into ethanol, the separated crystals were filtered off and washed with ethanol/ether. The resulting crude product was thereupon chromatographed on LiChroprep RP-18 with water and subsequently with water containing an increasing amount of methanol. Evaporation of the relevant fractions, brief boiling in 1N hydrochloric acid and filtration over a 0.8 μm cellulose filter yielded 4'-[4-[4-(4'-carboxy-biphenyl-4-yloxy)-phenylsulfonyl]-phenoxy]-biphenyl-4-carboxylic acid as a colourless powder, MS: m/z 641.2 ([M–H]$^-$).

B. Analogously to Example 6.A., from 4'-[4-[4-(4'-carboxy-biphenyl-4-yloxy)-phenylsulfonyl]-phenoxy]-biphenyl-4-carboxylic acid and D-glucamine there was obtained 4'-[4-[4-[4'-(D-glucit-1-ylcarbamoyl)-biphenyl- 4-yloxy]-phenylsulfonyl]-phenoxy]-biphenyl-4-carboxylic acid D-glucit-1-ylamide which was used directly in the next step.

C. The 4'-[4-[4-[4'-(D-glucit-1-ylcarbamoyl)-biphenyl-4-yloxy]-phenylsulfonyl]-phenoxy]-biphenyl-4-carboxylic acid D-glucit-1-ylamide obtained above was converted analogously to Example 1.B. into 4'-[4-[4-[4'-(2,3,4,5,6-penta-O-sulfo-D-glucit-1-ylcarbamoyl)-biphenyl-4-yloxy]-phenylsulfonyl]-phenoxy]-biphenyl-4-carboxylic acid 2,3,4,5,6-penta-O-sulfo-D-glucit-1-ylamide decasodium salt, $[\alpha]_D^{20}$ –4.3° (c 0.6; water), MS: m/z 1989.0 (reconstructed M).

Example 50

A. Analogously to Example 5.B., from 5,5'-(methylene-bis-oxymethylene)-di-furan-2-carboxylic acid and D-glucamine there was obtained 5,5'-(methylene-bis-oxymethylene)-di-furan-2-carboxylic acid bis-D-glucit-1-ylamide as a white powder, MS: m/z 623.4 ([M+H]$^+$).

B. The 5,5'-(methylene-bis-oxymethylene)-di-furan-2-carboxylic acid bis-D-glucit-1-ylamide obtained above was converted analogously to Example 1.B. into 5,5'-(methylene-bis-oxymethylene)-di-furan-2-carboxylic acid bis-(2,3,4,5,6-penta-O-sulfo-D-glucit-1-yl-amide) decasodium salt, $[\alpha]_D^{20}$ −2.2° (c 0.6; water), MS: m/z 1642.5 (reconstructed M).

Example 51

A. A solution of 3.15 g of 1-(4-amino-phenyl)-3-(2,3,4,5,6-penta-O-acetyl-D-glucit- 1-yl)-urea (see Example 7.B.) and 0.63 g of oxalic acid diimidazolide in 30 ml of acetone was stirred at room temperature for 2 hours and then evaporated. The residue was chromatographed on silica gel with methylene chloride/isopropanol and gave N,N'-bis-[4-[3-(penta-O-acetyl-D-glucit-1-yl)-ureido]-phenyl]-oxalamide, $[\alpha]_D^{20}$ −21.2° (c 0.5; chloroform), MS: m/z 1105.7 ([M+H]$^+$).

B. A solution of N,N'-bis-[4-[3-(penta-O-acetyl-D-glucit-1-yl)-ureido]-phenyl]-oxalamide obtained above was dissolved in the presence of 1 ml of 2% methanolic sodium methylate solution at room temperature for 4 hours. The resulting precipitate was filtered off under suction, rinsed with methanol and ether and dried at 60° C. There was obtained N,N'-bis-[4-[3-(D-glucit-1-yl)-ureido]-phenyl]-oxalamide, $[\alpha]_D^{20}$ −15.4° (c 0.5; dimethyl sulfoxide), MS: m/z 685,2 ([M+H]$^+$)

C. Sulfation of N,N'-bis-[4-[3-(D-glucit-1-yl)-ureido]-phenyl]-oxalamide as described under 1.B. yielded N,N'-bis-[4-[3-(2,3,4,5,6-penta-O-sulfo-D-glucit- 1-yl)-ureido]-phenyl]-oxalamide decasodium salt, $[\alpha]_D^{20}$ +3.6° (c 0.5; water), MS: m/z 1705.5 (reconstructed M).

Example 52

A. Reaction of Z-stilbene-4,4'-dicarboxylic acid and tris(hydroxymethyl)-aminomethane as described under Example 2.A. gave Z-stilbene-4,4'-dicarboxylic acid bis-(2-hydroxy-1,1-bis-hydroxymethyl-ethylamide), MS: m/z 475.4 ([M+H]$^+$).

B. Sulfation of Z-stilbene-4,4'-dicarboxylic acid bis-(2-hydroxy-1,1-bis-hydroxymethyl-ethylamide) as described under Example 1B yielded Z-stilbene-4,4'-dicarboxylic acid bis-(2-hydroxysulfonyloxy-1,1-bis-hydroxysulfonyloxymethyl-ethylamide) hexasodium salt, MS: m/z 1086.8 (reconstructed M).

Example 53

A. 18.2 g of 5-hydroxy-isophthalic acid were stirred at reflux for 18 hours in 300 ml of methanol with the addition of 5 ml of sulfuric acid (96%). After cooling to 5° C. the mixture was adjusted to pH 8 with saturated sodium bicarbonate solution, and the methanol was then distilled off in a water-jet vacuum. The heterogeneous residue was exhaustively extracted with methylene chloride. The organic phase was dried over magnesium sulfate, filtered and concentrated and yielded dimethyl 5-hydroxy-isophthalate which was recrystallized from methylene chloride/n-hexane, melting point 159°–161° C.

B. 1.043 g of solid di-tert.-butyl azodicarboxylate were added at −10° C. to a solution of 0.690 g of dimethyl 5-hydroxy-isophthalate, 0.582 g of biphenyl-4-yl-methanol and 1.182 g of triphenylphosphine in 40 ml of tetrahydrofuran. The reaction mixture was stirred under argon at 0° C. for 1 hour and at room temperature for a further 16 hours. Subsequently, the reaction mixture was filtered, the filter residue was washed with methylene chloride and the filtrate was evaporated. The resulting residue was chromatographed on silica gel with methylene chloride. There was thus obtained dimethyl 5-biphenyl-4-ylmethoxy-isophthalate, m.p. 118°–119° C.

C. 1.03 g of dimethyl 5-biphenyl-4-ylmethoxy-isophthalate were stirred at room temperature in 12 ml of 1N sodium hydroxide solution and 6 ml of acetonitrile for 16 hours. The reaction mixture was concentrated under reduced pressure, diluted with water, acidified with dilute KHSO$_4$ solution and filtered. There was thus obtained 5-biphenyl-4-ylmethoxy-isophthalic acid, MS: m/z 347.3 ([M−H]$^-$).

D. Analogously to Example 6.A. from 5-biphenyl-4-ylmethoxy-isophthalic acid and D-glucamine there was obtained 5-biphenyl-4-ylmethoxy-N,N'-di-D-glucit- 1-yl-isophthalamide as a white powder, MS: m/z 675.4 ([M+H]$^+$).

E. The 5-biphenyl-4-ylmethoxy-N,N'-di-D-glucit-1-yl-isophthalamide obtained above was converted analogously to Example 1.B. into 5-biphenyl-4-ylmethoxy-N,N'-bis-( 2,3,4,5,6-penta-O-sulfo-D-glucit-1-yl)-isophthalamide decasodium salt, $[\alpha]_D^{20}$ −6.5° (c 0.8, water).

Example 54

A. Reaction of 4,4'-ethynylenedibenzoic acid (Tetrahedron Lett. 32, 3117 (1967)) and D-glucamine as described under Example 3.A. gave 4,4'-ethynylenedibenzoic acid bis-D-glucit-1-ylamide, $[\alpha]_D^{20}$ −3.2° (c 0.5; DMSO), MS: m/z 593.5 ([M+H]$^+$).

B. Sulfation of 4,4'-ethynylenedibenzoic acid bis-D-glucit-1-ylamide as described under Example 2.B. gave 4,4'-ethynylenedibenzoic acid bis-(2,3,4,5,6-penta-O-sulfo-D-glucit-1-ylamide) decasodium salt, $[\alpha]_D^{20}$ −5.6° (c 0.5; water), MS: m/z 1613.0 (reconstructed M).

Example 55

A. A solution of 0.4 g of bis-(4-hydroxyphenyl)-methane in 8 ml of acetonitrile was treated under argon with 0.3 g of powdered potassium carbonate and 0.4 g of tert-butyl bromoacetate and stirred at room temperature for 2.5 hours. An additional 0.13 g of tert-butyl bromoacetate was added and the mixture was stirred at room temperature for 70 hours. The reaction mixture was concentrated and the residue was chromatographed on silica gel with methylene chloride/ether (95:5) and yielded di-tert-butyl 4,4'-methylene-bis-phenoxyacetate as a colourless solid, MS: m/z 428 ([M]$^+$).

B. A solution of 1.0 g of di-tert-butyl 4,4'-methylene-bis-phenoxyacetate in 18 ml of dioxan was treated with 3 ml of trifluoroacetic acid and 3 ml of water and stirred at 110° C. for 8 hours. Subsequently, the reaction mixture was concentrated and treated with water. The separated crystals were filtered off, yielding 4,4'-methylene-bis-phenoxyacetic acid as a colourless solid, MS: m/z 316 ([M]$^+$).

C. Analogously to Example 6.A., from 4,4'-methylene-bis-phenoxyacetic acid and D-glucamine there was obtained N-D-glucit-1-yl-2-[4-(4-D-glucit- 1-ylcarbamoylmethoxy-benzyl)-phenoxy]-acetamide as a colourless solid, MS: m/z 665.3 ([M+Na]$^+$).

D. The N-D-glucit-1-yl-2-[4-(4-D-glucit-1-yl-carbamoyl-methoxy-benzyl)-phenoxy]-acetamide obtained above was converted analogously to Example 1.B. into N-(2,3,4,5,6-penta-O-sulfo-D-glucit-1-yl)-2-[4-[4-(2,3,4,5,6-penta-O- sulfo-D-glucit-1-ylcarbamoylmethoxy)-benzyl]-phenoxy]-acetamide $[\alpha]_D^{20}$ +5.4° (c 0.5, water); MS: m/z 1663.0 (reconstructed M).

Example 56

A. 1.1 g of 3,5-dinitrobenzyl chloride, 0.85 g of 4-hydroxybiphenyl and 0.7 g of finely ground potassium carbonate in 10 ml of acetonitrile were heated at 50° C. under argon for 2.5 hours and subsequently under reflux for a further 8 hrs. Subsequently, the mixture was filtered and the filtrate was concentrated. The resulting residue was chromatographed on silica gel with methylene chloride/hexane (9:1). There was thus obtained 4-(3,5-dinitro-benzyloxy)-biphenyl as a yellowish solid; elementary analysis calculated for $C_{19}H_{14}N_2O_5$: C=65.14%, H=4.03%, N=8.00%; found: C=64.84%, H=4.04%, N=7.79%.

B. 2.65 g of 4-(3,5-dinitro-benzyloxy)-biphenyl in 30 ml of ethyl acetate were exhaustively hydrogenated in a hydrogen atmosphere with the addition of 200 mg of platinum oxide. Subsequently, the reaction mixture was filtered over Dicalite and the filtrate was concentrated. The residue was recrystallized from ether/hexane and yielded 5-(biphenyl-4-yloxymethyl)-benzene-1,3-diamine in the form of colourless crystals, MS: m/z 290 ($[M]^+$).

C. A solution of 1.0 g of 5-(biphenyl-4-yloxymethyl)-benzene-1,3-diamine in 25 ml of tetrahydrofuran was treated with 0.97 ml of triethylamine and 690 mg of triphosgene under argon and while cooling with ice and subsequently stirred at room temperature for 4 hours. The mixture was filtered, the residue was concentrated, dissolved in 20 ml of dimethylformamide, treated with 1.3 g of D-glucamine and stirred at room temperature for 18 hours. Subsequently, the mixture was again concentrated, treated with 50 ml of pyridine and 50 ml of acetic anhydride and stirred for a further 18 hours. Thereupon, the reaction mixture was again concentrated, treated with ice-water and 1N hydrochloric acid and extracted with methylene chloride. The methylene chloride phases were dried over magnesium sulfate and concentrated. The residue was chromatographed on silica gel with ethyl acetate. The product fractions were subsequently dissolved in 25 ml of methanol and 10 ml of tetrahydrofuran, treated with 1 ml of 1 molar sodium methylate solution in methanol and stirred at room temperature for a further 18 hours. The separated precipitate was filtered off and, for further purification, again acetylated with 25 ml of pyridine and 25 ml of acetic anhydride. The crude product was chromatographed on silica gel with methylene chloride/isopropanol (91:9). There thereby resulted 3,3'-bis-(2,3,4,5,6-penta-O-acetyl-D-glucit-    1-yl)-1,1'-(5-biphenyl-4-yloxymethyl-benzene-1,3-diyl)-diurea as a colourless foam, MS: m/z 1142.6 ($[M+NH_4]^+$).

D. A solution of 0.68 g of 3,3'-bis-(2,3,4,5,6-penta-O-acetyl-D-glucit-1-yl)-1,1'-(5-biphenyl-4-yloxymethyl-benzene-1,3-diyl)-diurea in 10 ml of methanol and 4 ml of tetrahydrofuran was treated with 0.5 ml of 1 molar sodium methylate solution in methanol and stirred at room temperature for 2 hours. The separated precipitate was filtered off and yielded 3,3'-di-D-glucit-1-yl-1,1'-(5-biphenyl-4-yloxymethyl-benzene- 1,3-diyl)-diurea as a colourless solid, MS: m/z 705.4 ($[M+H]^+$).

E. The 3,3'-di-D-glucit-1-yl-1,1'-(5-biphenyl-4-yloxymethyl-benzene- 1,3-diyl)-diurea obtained above was converted analogously to Example 1.B. into 3,3'-bis-(2,3,4,5,6-penta-O-sulfo-D-glucit-1-yl)-1,1'-(5-biphenyl-4-yloxymethyl-benzene-1,3-diyl)-diurea  decasodium  salt, $[\alpha]_D^{20}$ −0.86° (c 0.7, water), MS: m/z 1726.0 (reconstructed M).

Example 57

A. 0.581 mg of 5-(biphenyl-4-yloxymethyl)-benzene-1, 3-diamine, 0.4 g of maleic anhydride, 40 mg of 4-dimethylaminopyridine and 0.6 ml of triethylamine were stirred under argon in 18 ml of methylene chloride for 18 hrs. Thereupon, the reaction mixture was concentrated. The residue was treated with water and extracted with ethyl acetate. The product was separated from the aqueous phase by the addition of 1N hydrochloric acid. After filtration and drying there was obtained (Z)-3-[3-biphenyl-4-yloxymethyl-5-[(Z)-3-carboxy-acryloylamino]-phenylcarbamoyl]-acrylic acid as a brownish solid, MS: m/z 485.3 ($[M−H]^−$)

B. A suspension of 0.94 g of (Z)-3-[3-biphenyl-4-yloxymethyl-5-[(Z)-3-carboxy-acryloylamino]-phenylcarbamoyl]-acrylic acid in 10 ml of dimethylformamide was treated with 0.45 ml of 4-methylmorpholine at 0°–5° C. with the exclusion of moisture and stirred intensively for 10 minutes. Thereupon, 0.702 g of solid 2-chloro-4,5-dimethoxy-1,3,5-triazine was added and the mixture was stirred at 0°–5° C. for 2 hours. After the addition of 0.727 g of D-glucamine the mixture was stirred at room temperature for 18 hours. Thereupon, the reaction mixture was diluted several times with water and evaporated at 40°–50° C. under reduced pressure, treated with 40 ml of pyridine and 50 ml of acetic anhydride and stirred for a further 18 hrs. The reaction mixture was again concentrated and treated with ice-water and 1N hydrochloric acid. The resulting precipitate was filtered off and chromatographed on silica gel with methylene chloride/isopropanol. There thereby resulted (Z)-butenedicarboxylic acid-(Z)-1-[3-biphenyl-4-yloxymethyl-5-[3-(2, 3,4,5,6-penta-O-acetyl-D-glucit-1-ylcarbamoyl)-acryloylamino]-phenylamide] 4-(2,3,4,5,6-penta-O-acetyl-D-glucit-1-ylamide) as a brownish solid, MS: m/z 1250.6 ($[M+NH_4]^+$)

C. 0.188 g of (Z)-butenedicarboxylic acid-(Z)-1-[3-biphenyl-4-yloxymethyl- 5-[3-(2,3,4,5,6-penta-O-acetyl-D-glucit-1-ylcarbamoyl)-acryloylamino]-phenylamide] 4-(2,3,4, 5,6-penta-O-acetyl-D-glucit-1-ylamide) in 15 ml of ethyl acetate were exhaustively hydrogenated in a hydrogen atmosphere with the addition of 30 mg of palladium on charcoal (10%). Subsequently, the reaction mixture was filtered over Dicalite and concentrated. This yielded N1-(2,3,4,5,6-penta-O-acetyl-D-glucit- 1-yl)-N4-[5-biphenyl-4-yloxymethyl-3-[3-(2,3,4,5,6-penta-O-acetyl-D-glucit- 1-ylcarbamoyl)-propionylamino]-phenyl]-succinamide as a colourless solid; MS: m/z 1259.7 ($[M+Na]^+$).

D. A solution of 0.17 g of N1-(2,3,4,5,6-penta-O-acetyl-D-glucit-1-yl)-N4-[5-biphenyl-4-yloxymethyl-3-[3-(2,3,4, 5,6-penta-O-acetyl-D-glucit-    1-ylcarbamoyl)-propionylamino]-phenyl]-succinamide in 10 ml of methanol was treated with 10 mg of anhydrous sodium carbonate and stirred at room temperature overnight. The resulting precipitate was filtered off and washed with methanol and yielded N1-[5-biphenyl-4-yloxymethyl-3-(3-D-glucit-1-ylcarbamoyl-propionylamino)-phenyl]-N4-D-glucit-1-yl-succinamide as a brownish solid; MS: m/z 839.6 ($[M+Na]^+$).

E. The N1-[5-biphenyl-4-yloxymethyl-3-(3-D-glucit-1-ylcarbamoyl-propionylamino)-phenyl]-N 4-D-glucit-1-yl-succinamide obtained above was converted analogously to Example 1.B. into N1-[3-biphenyl-4-yloxymethyl- 5-[3-(2, 3,4,5,6-penta-O-sulfo-D-glucit-1-ylcarbamoyl)-propionylamino]-phenyl]-N4-(2,3,4,5,6-penta-O-sulfo-D-glucit-1- yl)-succinamide decasodium salt, $[\alpha]_D^{20}$ −4.4° (c 0.5, water), MS: m/z 1837.5 (reconstructed M).

Example 58

A. A suspension of 0.98 g of (Z)-3-[3-biphenyl-4-yloxymethyl-5-[(Z)-3-carboxy-acryloylamino]-phenylcarbamoyl]-acrylic acid in 10 ml of dimethylformamide was treated with 0.5 ml of 4-methylmorpholine at 0°–5° C. with the exclusion of moisture and stirred intensively for 10 minutes. Thereupon, 0.75 g of solid 2-chloro-4,6-dimethoxy-1,3,5-triazine was added and the reaction mixture was stirred at 0°–5° C. for a further 2 hours. After the addition of 0.75 g of D-glucamine the mixture was stirred at room temperature for a further 18 hours. Thereupon, the reaction mixture was diluted several times with water and evaporated at 40°–50° C. under reduced pressure. The resulting crude product was thereupon chromatographed on LiChroprep RP-18 silica gel with water and subsequently with water containing increasing amounts of methanol. Evaporation of the relevant fractions and drying at 50° C. in a vacuum yielded (Z)-butenedioic acid (Z)-[3-biphenyl-4-yloxymethyl- 5-(3-D-glucit-1-ylcarbamoyl-acryloylamino)-phenylamide]-D-glucit-1-ylamide as a brownish powder, MS: m/z 835.2 ([M+Na]⁺).

B. The (Z)-butenedioic acid (Z)-[3-biphenyl-4-yloxymethyl-5-(3-D-glucit- 1-ylcarbamoyl-acryloylamino)-phenylamide]-D-glucit-1-ylamide obtained above was converted analogously to Example 1.B. into (Z)-butenedioic acid (Z)-[3-biphenyl-4-yloxymethyl-5-[3-(2,3,4,5,6-penta-O-sulfo-D-glucit- 1-ylcarbamoyl)-acryloylamino]-phenylamide]-(2, 3,4,5,6-penta-O-sulfo-D-glucit-1-yl)-amide decasodium salt, $[\alpha]_D^{20}$ −3.4° (c 0.5, water); MS: m/z 1834.0 (reconstructed M).

Example 59

A. 3.00 g of 2,3:4,5-di-O-isopropylidene-1-O-(4-methylphenylsulfonyl)-D-arabinitol, 0.94 g of 9,9-dimethyl-9H-xanthene-3,6-diol and 5.38 g of potassium carbonate were stirred at reflux in 130 ml of dimethylformamide for 3 hours. The reaction mixture was treated with ice-water and extracted with methylene chloride. The combined methylene chloride phases were dried over magnesium sulfate and concentrated. Thereupon, the crude product was chromatographed on silica gel with hexane, methylene chloride and methanol. There was obtained 2,3:2',3':4,5:4',5'-tetra-O-isopropylidene-1,1'-O-(9,9-dimethyl-9H-xanthene-3,6-diyl)-di-D-arabinitol, MS: m/z 655 ([M−CH₃]⁺).

B. 1.80 g of 2,3:2',3':4,5:4',5'-tetra-O-isopropylidene-1,1'-O-(9,9-dimethyl- 9H-xanthene-3,6-diyl)-di-D-arabinitol were stirred at reflux in 70 ml of dioxan with 12 ml of trifluoroacetic acid (50% in water) for 3 hours. After cooling to room temperature the mixture was concentrated, the residue was treated twice with 50 ml of toluene and again concentrated; the thus-obtained residue was taken up in 50 ml of water, stirred at room temperature for 1 hour, then cooled to 10° C. and filtered off. After drying over phosphorus pentoxide at 50° C. there was obtained 1,1'-O-(9,9-dimethyl-9H-xanthene-3,6-diyl)-di-D-arabinitol; IR (KBr, cm⁻¹): 3394, 1613, 1502, 1262, 1180, 1041, 833.

C. 1.02 g 1,1'-O-(9,9-dimethyl-9H-xanthene-3,6-diyl)-di-D-arabinitol were reacted with sulfur trioxide trimethylamine complex in analogy to Example 1.B. There was thus obtained 2,2',3,3',4,4',5,5'-octa-O-sulfo-1,1'-O-(9,9-dimethyl-9H-xanthene-3,6-diyl)-di-D-arabinitol octasodium salt, MS: m/z 1327.5 (reconstructed M).

Example 60

A. A solution of 0.47 g of 3,6,9-trioxaundecanedioic acid in 10 ml of acetonitrile was treated with 0.44 ml of 4-methylmorpholine at 0°–5° C. with the exclusion of moisture and stirred intensively for 10 minutes. Thereupon, 0.70 g of solid 2-chloro-4,6-dimethoxy-1,3,5-triazine was added and the mixture was stirred at 0°–5° C. for a further 2 hours. Subsequently, a solution of 1.29 g of 1-O-(4-amino-phenyl)-2,3:4,5-di-O-isopropylidene-D-arabinitol (example 12.B) in 30 ml of acetonitrile/dimethylformamide (2:1) was added and the mixture was stirred at room temperature for a further 18 hours. After distillation of the solvent in a high vacuum the residue was chromatographed on silica gel with methylene chloride and methanol. This yielded 3,6,9-trioxaundecanedioic acid bis-[4-(2,3:4,5-di-O-isopropylidene-D-arabinit-1-yloxy)-phenylamide], MS: m/z 833 ([M+H]⁺).

B. 1.12 g of 3,6,9-trioxaundecanedioic acid bis-[4-(2,3:4, 5-di-O-isopropylidene-D-arabinit- 1-yloxy)-phenylamide] were reacted in analogy to Example 12.D. and worked up. There was obtained 3,6,9-trioxaundecanedioic acid bis-(4-D-arabinit-1-yloxy-phenylamide); IR (KBr, cm⁻¹): 3410, 3264, 1661, 1514, 1236, 1112, 1043, 825.

C. 3,6,9-trioxaundecanedioic acid bis-(4-D-arabinit-1-yloxy-phenylamide) was reacted with sulfur trioxide trimethylamine complex in analogy to Example 1.B. There was thus obtained 3,6,9-trioxaundecanedioic acid bis-[4-(2,3,4, 5-tetra-O-sulfo-D-arabinit-1-yloxy)-phenylamide] octasodium salt, MS: m/z 1489.5 (reconstructed M).

Example 61

A. 4,4'-Dihydroxy-biphenyl and 2,3:4,5-Di-O-isopropylidene-1-O-(4-methyl-phenylsulfonyl)-D-arabinitol were reacted in analogy to Example 59.A. and worked up. The crude product was chromatographed on silica gel with methylene chloride and methanol and yielded 2,3:2',3':4, 5:4',5'-tetra-O-isopropylidene-1,1'-O-biphenyl-4,4'-diyl-di-D-arabinitol, MS: m/z 614 ([M]⁺).

B. 0.98 g of 2,3:2',3':4,5:4',5'-tetra-O-isopropylidene-1,1'-O-biphenyl- 4,4'-diyl-di-D-arabinitol was stirred at reflux for 6 hours with 6 ml of trifluoroacetic acid (70% in water) and 15 ml of dioxan in analogy to Example 12.D. After cooling the reaction mixture to room temperature it was filtered; the residue was washed twice with 5 ml of ethyl acetate each time and dried at 50° C. over phosphorus pentoxide in a high vacuum. There was obtained 1,1'-O-biphenyl-4,4'-diyl-di-D-arabinitol, MS: m/z 455 ([M]⁺).

C. 0.55 g of 1,1'-O-biphenyl-4,4'-diyl-di-D-arabinitol was reacted with sulfur trioxide trimethylamine complex in analogy to Example 1.B. There was thus obtained 2,2',3,3', 4,4',5,5'-octa-O-sulfo-1,1'-O-biphenyl-4,4'-diyl-di-D-arabinitol octasodium salt, MS: m/z 1271.0 (reconstructed M).

Example 62

A. 2,3:4,5-Di-O-isopropylidene-1-O-(4-methyl-phenylsulfonyl)-D-arabinitol and 4,4'-ethynediyl-diphenol were reacted in analogy to Example 59.A. and worked up. The crude product was chromatographed on silica gel with hexane, methylene chloride and acetonitrile. There was obtained 2,3:2',3':4,5:4',5'-tetra-O-isopropylidene-1,1'-O-( 4,4'-ethynediyl-diphenylene)-di-D-arabinitol, MS: m/z 638 ([M]⁻).

B. 1.57 g of 2,3:2',3':4,5:4',5'-tetra-O-isopropylidene-1,1'-O-( 4,4'-ethynediyl-diphenylene)-di-D-arabinitol were reacted in analogy to Example 59.B. with 25 ml of trifluoroacetic acid (60% in water) in 50 ml of dioxan and worked up. There was thus obtained 1,1'-O-(4,4'-ethyndiyl-diphenylene)-di-D-arabinitol, elementary analysis calculated for $C_{24}H_{30}O_{10}$: C=60.24%, H=6.32%; found: C=59.98%, H=6.35%.

C. 1.00 g of 1,1'-O-(4,4'-ethynediyl-diphenylene)-di-D-arabinitol were reacted with sulfur trioxide trimethylamine complex in analogy to Example 1.B. There was thus obtained 2,2',3,3',4,4',5,5'-octa-O-sulfo-1,1'-O-(4,4'-ethynediyl-diphenylene)-di-D-arabinitol octasodium salt, MS: m/z 1294.5 (reconstructed M).

Example 63

0.40 g of 2,2',3,3',4,4',5,5'-octa-O-sulfo-1,1'-O-(4,4'-ethynediyl-diphenylene)-di-D-arabinitol octasodium salt, were hydrogenated in 12 ml of water with 0.1.6 g of Lindlar catalyst with the addition of 1.5 ml of pyridine. After filtering off the catalyst, the filtrate was lyophilized and gave (Z)-2,2',3,3',4,4',5,5'-octa-O-sulfo-1,1'-O-( 4,4'-ethylene-diphenylene)-di-D-arabinitol octasodium salt, MS: m/z 1296.5 (reconstructed M).

Example 64

0.42 g of 2,2',3,3',4,4',5,5'-octa-O-sulfo-1,1'-O-(4,4'-ethynediyl-diphenylene)-di-D-arabinitol octasodium salt in 10 ml of water were reduced by catalytic hydrogenation with 0.17 g of palladium on charcoal (10%). After filtering off the catalyst, the filtrate was lyophilized and gave 2,2',3,3',4,4',5,5'-octa-O-sulfo-1,1'-O-(4,4'-ethane-1,2-diyl-diphenylene)-di-D-arabinitol octasodium salt, MS: m/z 1299.0 (reconstructed M).

Example 65

A. 24.50 g of 1,2:3,4-di-O-isopropylidene-alpha-D-galactopyranose were reacted with 19.7 g of p-toluenesulfonyl chloride at room temperature for 18 hours with the addition of 0.12 g of 4-dimethylaminopyridine in 200 ml of pyridine. The reaction mixture was treated with ice-water and extracted with methylene chloride. The organic phase was washed twice with water, dried over magnesium sulfate, filtered and concentrated. The crude product was chromatographed on silica gel with methylene chloride and methanol. There was obtained 1,2:3,4-di-O-isopropylidene-6-O-(p-tolylsulfonyl)-alpha-D-galactopyranose, which was recrystallized from n-hexane, m.p.: 91°–92° C.

B. 18.64 g of 1,2:3,4-di-O-isopropylidene-6-O-(p-tolylsulfonyl)-alpha-D-galactopyranose and 6.85 g of 4-nitrophenol were reacted in analogy to Example 59.A. The thus-obtained crude product was chromatographed on silica gel with n-hexane and methylene chloride. There was obtained 1,2:3,4-di-O-isopropylidene-6-O-(4-nitro-phenyl)-alpha-D-galactopyranose, MS: m/z 381 ([M]$^+$).

C. 13.60 g of 1,2:3,4-di-O-isopropylidene-6-O-(4-nitro-phenyl)-alpha-D-galactopyranose were hydrogenated in 150 ml of methanol with 3.0 g of palladium on charcoal. The catalyst was filtered off and washed twice with methanol. The filtrate was concentrated and gave 1,2:3,4-di-O-isopropylidene-6-O-(4-amino-phenyl)-alpha-D-galactopyranose, MS: m/z 351 ([M]$^+$).

D. 4.35 g of 1,2:3,4-di-O-isopropylidene-6-O-(4-amino-phenyl)-alpha-D-galactopyranose were reacted at room temperature for 16 hours with 3.72 g of dibenzyl dicarbonate and 6.20 ml of triethylamine in 150 ml of dioxan/water 2:1. The reaction mixture was treated with ice-water and extracted with methylene chloride. The organic phase was washed with water, dried over magnesium sulfate, filtered and concentrated. The resulting crude product was chromatographed on silica gel with n-hexane, methylene chloride and acetonitrile and yielded 6-O-(4-benzyloxycarbonyl-amino-phenyl)-1,2:3,4-di-O-isopropylidene-alpha-D-galactopyranose, MS: m/z 485 ([M]$^+$).

E. 1.49 g of 6-O-(4-benzyloxycarbonylamino-phenyl)-1, 2:3,4-di-O-isopropylidene-alpha-D-galactopyranose were stirred at reflux for 3 hours with 15 ml of trifluoroacetic acid (35% in water) and 20 ml of dioxan in analogy to Example 12.D. After distillation of the solvent in a high vacuum the residue was recrystallized from methanol and ether and yielded 6-O-(4-benzyloxycarbonylamino-phenyl)-D-galactose, MS: m/z 406 ([M+H]$^+$).

F. 3.60 g of 6-O-(4-benzyloxycarbonylamino-phenyl)-D-galactose were stirred at room temperature for 65 hours with 1.40 g of sodium borohydride in 125 ml of methanol. After hydrolysis and neutralization of the reaction mixture, the reaction mixture was concentrated. The residue was dried over phosphorus pentoxide in a high vacuum for 4 hours. For purification, the residue was converted with acetic anhydride in pyridine into the corresponding pentaacetyl derivative and this was chromatographed on silica gel with methylene chloride. There was thus obtained 1,2,3,4,5-penta-O-acetyl-6-O-(4-benzyloxycarbonylamino-phenyl)-D-galactitol, which was used directly in the next step.

G. 5.20 g of 1,2,3,4,5-penta-O-acetyl-6-O-(4-benzyloxycarbonylamino-phenyl)-D-galactitol were hydrogenated in 150 ml of tetrahydrofuran with 1.0 g of palladium on charcoal (10%). After filtration the solvent was distilled off. The residue was recrystallized from methylene chloride and n-hexane. There was thus obtained 1,2,3,4,5-penta-O-acetyl-6-O-(4-amino-phenyl)-D-galactitol, which was used directly in the next step.

H. 3.37 g of 1,2,3,4,5-penta-O-acetyl-6-O-(4-amino-phenyl)-D-galactitol in 250 ml of methanol were stirred at room temperature for as 18 hours with 5.30 ml of sodium methylate solution (5.4 molar in methanol). After neutralization of the reaction mixture with 2N hydrochloric acid the solvent was distilled off. The crude product was taken up in 50 ml of water, stirred at room temperature for 15 minutes, then filtered and washed twice with 10 ml of water each time. The residue was stirred at reflux in 100 ml of 2N hydrochloric acid for 3 hours and then concentrated. This residue was dried over phosphorus pentoxide at room temperature in a high vacuum for 6 hours and yielded 6-O-(4-amino-phenyl)-D-galactitol hydrochloride, MS: m/z 273 ([M]$^+$).

I. 1.24 g of 6-O-(4-amino-phenyl)-D-galactitohydrochloride in 40 ml of dimethylformamide were stirred at room temperature for 20 hours with 0.32 g of 1,1'-carbonyldiimidazole with the addition of 1.12 ml of triethylamine. The product was precipitated by the addition of water and was filtered off, washed twice with water and dried at 50° C. over phosphorus pentoxide in a high vacuum for 5 hours. There was obtained 1,3-bis-(4-D-galactit-6-yloxy-phenyl)-urea, MS: m/z 595 ([M+Na]$^+$).

K. 0.73 g of 1,3-bis-(4-D-galactit-6-yloxy-phenyl)-urea were reacted with sulfur trioxide trimethylamine complex in analogy to Example 1.B. There was obtained 1,3-bis-[4-(2,3,4,5,6-penta-O-sulfo-D-galactit-6-yloxy)-phenyl]-urea decasodium salt, MS: m/z 1593.0 (reconstructed M).

Example 66

A. 2.79 g of 2,3:4,5-di-O-isopropylidene-D-arabinitol were stirred at room temperature for 18 hours with 0.98 ml of propargyl bromide with the addition of 0.78 g of potassium hydroxide in 30 ml of tetrahydrofuran. After distillation of the solvent the crude product was chromatographed on silica gel with methylene chloride. There was thus obtained 2,3:4,5-di-O-isopropylidene-1-O-prop-2-yneyl-D-arabinitol, MS: m/z 255 ([M–CH$_3$]$^-$).

B. 2.06 g of 2,3:4,5-di-O-isopropylidene-1-O-prop-2-yneyl-D-arabinitol in 55 ml of 1,2-dichlorobenzene were stirred at 80° C. for 2 hours with 1.11 ml of N,N,N',N'-tetramethylethylenediamine, 0.07 g of copper(I) chloride and 11.1 g of molecular sieves (4 Å) while passing oxygen through the mixture. After distillation of the solvent the residue was chromatographed on silica gel with methylene chloride and methanol. There was thus obtained 2,3:2',3':4,5:4',5'-tetra-O-isopropylidene- 1,1'-O-hexa-2,4-diyne-1,6-diyl-di-D-arabinitol, MS: m/z 523 ([M–CH$_3$]$^+$).

C. 1.10 g of 2,3:2',3':4,5:4',5'-tetra-O-isopropylidene-1,1'-O-hexa-2,4-diyne- 1,6-diyl-di-D-arabinitol were reacted with 6.6 ml of trifluoroacetic acid (70% in water) in 35 ml of dioxan in analogy to Example 12.D. There was obtained 1,1'-O-hexa-2,4-diyne-1,6-diyl-di-D-arabinitol, which was used directly in the next step.

D. 0.75 g of 1,1'-O-hexa-2,4-diyne-1,6-diyl-di-D-arabinitol were reacted with sulfur trioxide trimethylamine complex in analogy to Example 1.B. There was thus obtained 2,2',3,3',4,4',5,5'-octa-O-sulfo-1,1'-O-hexa-2,4-diyne-1,6-diyl-di-D-arabinitol octasodium salt, MS: m/z 1194.5 (reconstructed M).

Example 67

A. A solution of 3.44 g of 4,4'-difluoro-3,3'-dinitrodiphenyl sulfone in 50 ml of absolute dimethylformamide and 3 ml of triethylamine was treated with 3.7 g of D-glucamine and stirred at room temperature for 5 hours. Then, 50 ml of methanol were added dropwise, the separated product was filtered off under suction, rinsed with methanol and dried. There was obtained N,N'-di-D-glucit-1-yl-2,2'-dinitro-4,4'-sulfonyldianiline as a yellow powder, $[\alpha]_D^{20}$ +12.2° (c 0.5; DMSO), MS: m/z 689.7 ([M+Na]$^+$).

B. Reaction of N,N'-di-D-glucit-1-yl-2,2'-dinitro-4,4'-sulfonyldianiline as described under Example 2.B. (sulfur trioxide triethylamine complex being used in place of sulfur trioxide trimethylamine complex) gave N,N'-bis-(2,3,4,5,6-penta-O-sulfo-D-glucit-1-yl)-2,2'-dinitro-4,4'-sulfonyldianiline decasodium salt as an orange powder, $[\alpha]_D^{20}$ –2.0° (c, 0.5; water), MS: m/z 1687.0 (reconstructed M).

Example 68

A. A solution of 7.4 g of 4-fluoro-3-nitrobenzoic acid in 100 ml of dimethylformamide was treated with 16.0 g of D-glucamine and stirred at room temperature for 4 hours. After the addition of 6 ml of triethylamine the mixture was stirred at 40° C. for a further 16 hours. The reaction solution was evaporated. The residue was stirred at room temperature for 5 hours with 400 ml of pyridine and 200 ml of acetic anhydride. After concentration the residue obtained was treated with water and acidified to pH 2–3 with 5% hydrochloric acid solution and extracted with ethyl acetate. The organic extracts were washed with ice-water and saturated sodium chloride solution, dried over magnesium sulfate and evaporated. The residue was chromatographed over silica gel with ethyl acetate. The product fractions were concentrated, crystallized from ether and gave 4-(2,3,4,5,6-penta-O-acetyl-D-glucit- 1-ylamin)-3-nitrobenzoic acid as yellow crystals, $[\alpha]_D^{20}$ –23.0° (c 0.5; DMSO), MS: m/z 579.7 ([M+Na]$^+$).

B. A solution of 1.12 g of 4-(2,3,4,5,6-penta-O-acetyl-D-glucit-1-ylamin)-3-nitrobenzoic acid in 6 ml of dimethylformamide and 0.23 ml of N-methylmorpholine was treated at 0° C. with 385 mg of 2-chloro- 4,6-dimethoxy-1,3,5-triazine and stirred for 2 hours. After the addition of 198 mg of 4,4'-diamino-diphenylmethane the mixture was stirred at room temperature for 18 hours and concentrated. The residue was treated with ice-water and extracted with ethyl acetate. The extracts were washed with ice-water and saturated sodium chloride solution, dried over magnesium sulfate and evaporated. The residue was chromatographed over silica gel with methylene chloride/isopropanol and gave 4,4'-bis-(2,3,4,5,6-penta-O-acetyl-D-glucit-1-ylamino)-3,3'-dinitro-N,N'-(4,4'-methylene-diphenyl)-dibenzamide as a yellow powder, $[\alpha]_D^{20}$ –6.8° (c 0.5; DMSO), MS: m/z 1298.3 ([M+Na]$^+$).

C. A solution of 1.3 g of 4,4'-bis-(2,3,4,5,6-penta-O-acetyl-D-glucit-1-ylamino)- 3,3'-dinitro-N,N'-(4,4'-methylene-diphenyl)-dibenzamide in 13 ml of tetrahydrofuran and 15 ml of methanol was stirred at room temperature for 5 hours with 1.3 ml of 2% methanolic sodium methanolate solution. The precipitate was filtered off under suction, washed with methanol, dried and gave 4'-bis-D-glucit-1-ylamino-3,3'-dinitro-N,N'-( 4,4'-methylene-diphenyl)-dibenzamide as a yellow-orange powder, $[\alpha]_D^{20}$ +24.0° (c 0.5; DMSO), MS: m/z 877.7 ([M+Na]$^+$).

D. Reaction of 4,4'-bis-D-glucit-1-ylamino-3,3'-dinitro-N,N'-(4,4'-methylene-diphenyl)-dibenzamide as described under Example 67.B. gave 4,4'-bis-(2,3,4,5,6-penta-O-sulfo-D-glucit-1-ylamino)-3,3'-dinitro-N,N'-( 4,4'-methylene-diphenyl)-dibenzamide decasodium salt as a yellow-orange powder, $[\alpha]_D^{20}$ +8.2° (c 0.5; water), MS: m/z 1875.0 (reconstructed M).

Example 69

A. Reaction of 4-(2,3,4,5,6-penta-O-acetyl-D-glucit-1-ylamino)-3-nitrobenzoic acid with 1,3-diaminobenzene as described under Example 68.B. gave 4,4'-bis-(2,3,4,5,6-penta-O-acetyl-D-glucit-1-ylamino)-3,3'-dinitro-N,N'-benzene- 1,3-diyl-dibenzamide, $[\alpha]_D^{20}$ –6.6° (c 0.5; DMSO), MS: m/z 1207.6 ([M+Na]$^+$).

B. Reaction of 4,4'-bis-(2,3,4,5,6-penta-O-acetyl-D-glucit-1-ylamino)-3,3'-dinitro-N,N'-benzene-1,3-diyl-dibenzamide as described under Example 68.C. gave 4,4'-bis-D-glucit-1-ylamino-3,3'-dinitro-N,N'-benzene- 1,3-diyl-dibenzamide, $[\alpha]_D^{20}$ +27.4° (c 0.5; DMSO), MS: m/z 787.5 ([M+Na]$^+$).

C. Reaction of 4,4'-bis-D-glucit-1-ylamino-3,3'-dinitro-N,N'-benzene-1,3-diyl-dibenzamide as described under Example 67.B. gave 4,4'-bis-(2,3,4,5,6-penta-O-sulfo-D-glucit-1-ylamino)-3,3'-dinitro-N,N'-benzene-1,3-diyl-dibenzamide decasodium salt as a yellow-orange powder, $[\alpha]_D^{20}$ +9.8° (c 0.5; water), MS: m/z 1785.0 (reconstructed M).

Example 70

A. Reaction of 4-(2,3,4,5,6-penta-O-acetyl-D-glucit-1-ylamino)-3-nitrobenzoic acid with 1,3-diamino-propan-2-ol as described under Example 68.B. gave 4,4'-bis-(2,3,4,5,6-penta-O-acetyl-D-glucit-1-ylamino)- 3,3'-dinitro-N,N'-(2-hydroxy-propane-1,3-diyl)-dibenzamide, $[\alpha]_D^{20}$ –3.8° (c 0.5; DMSO), MS: m/z 1189.3 ([M+Na]$^+$).

B. Reaction of 4,4'-bis-(2,3,4,5,6-penta-O-acetyl-D-glucit-1-ylamino)-3,3'-dinitro-N,N'-(2-hydroxy-propane-1,3-diyl)-dibenzamide as described under Example 68.C. gave 4,4'-bis-D-glucit-1-ylamino-3,3'-dinitro-N,N'-( 2-hydroxypropane-1,3-diyl)-dibenzamide, $[\alpha]_D^{20}$ +27.2° (c 0.5; DMSO), MS: m/z 769 ([M+Na]$^+$).

C. Reaction of 4,4'-bis-D-glucit-1-ylamino-3,3'-dinitro-N,N'-(2-hydroxypropane- 1,3-diyl)-dibenzamide as described under Example 67.B. gave 4,4'-bis-(2,3,4,5,6-penta-O-sulfo-D-glucit-1-ylamino)-3,3'-dinitro-N,N'-( 2-hydroxysulfonyloxy-propane-1,3-diyl)-dibenzamide undecasodium salt as a yellow-orange powder, $[\alpha]_D^{20}$ +14.4° (c 0.5; water), MS: m/z 1869.0 (reconstructed M).

Example 71

A. A solution of 2.0 g of (Z)-stilbene-4,4'-dicarboxylic acid-bis-(2,3,4,5,6-penta-O-sulfo-D-glucit-1-ylamide) decasodium salt (see. Ex. 3) in 25 ml of methylene chloride was treated with 1.0 g of m-chlorobenzoic acid and stirred at room temperature for 5 hours. The reaction solution was poured onto ice-water and extracted with methylene chloride. The extracts were washed with water and sodium bicarbonate solution, dried and concentrated. The residue was chromatographed on silica gel with methylene chloride/isopropanol and gave cis-4,4'-oxiran-2,3-diyl-dibenzoic acid bis-(2,3,4,5,6-penta-O-acetyl-D-glucit- 1-ylamide), $[\alpha]_D^{20}$ +18.8° (c 0.5; chloroform), MS: m/z 1054.5 ([M+Na]$^+$).

B. A suspension of 1.6 g of cis-4,4'-oxirane-2,3-diyl-dibenzoic acid bis-(2,3,4,5,6-penta-O-acetyl-D-glucit-1-ylamide) in 25 ml of methanol was treated with 480 mg of potassium carbonate and stirred at room temperature for 3 hours. The reaction mixture was evaporated and purified over a "reversed phase" column (RP 18) with water/acetonitrile. Lyophilized product fractions gave pure cis-4,4'-oxirane- 2,3-diyl-dibenzoic acid bis-D-glucit-1-ylamide, $[\alpha]_D^{20}$ −7.0° (c 0.5; DMSO), MS: m/z 611.4 ([M+H]$^+$).

C. Sulfation of cis-4,4'-oxirane-2,3-diyl-dibenzoic acid bis-D-glucit-1-ylamide as described under Example 67.B. gave cis-4,4'-oxirane-2,3-diyl-dibenzoic acid bis-(2,3,4,5,6-penta-O-sulfo-D-glucit-1-ylamide) decasodium salt, $[\alpha]_D^{20}$ −4.0° (c 0.9; water), MS: m/z 1632.0 (reconstructed M).

Example 72

A. A solution of 38.0 g of (3-bromo-benzyl)-triphenylphosphonium bromide, known from the literature, in 250 ml of tetrahydrofuran was treated at −10° C. with 8.75 g of potassium tert.-butylate and stirred for 3 minutes. A solution of 14.8 g of 4-bromobenzaldehyde was added dropwise to the yellow-orange suspension within 15 minutes. After stirring for 60 minutes the reaction mixture was concentrated. The residue was treated with ice-water and extracted with ethyl acetate/ether. The organic phases were washed with water and saturated aqueous sodium chloride solution, dried over magnesium sulfate and evaporated. The residue was chromatographed over silica gel with hexane and hexane/ether 99:1 and gave (E)-3,4'-dibromostilbene as colourless crystals, MS: m/z 338 (M$^+$), as well as (Z)-3,4'-dibromostilbene as a colourless oil, MS: m/z 338 (M$^+$).

B. A solution of 3.38 g of (E)-3,4'-dibromostilbene in 200 ml of absolute ether was treated at −10° C. during 5–10minutes with 20 ml of a 1.6N butyllithium solution in hexane. After stirring for 3 hours the reaction solution was poured onto dry ice/ether and warmed slowly to 10° C. The ether solution was extracted several times with water. After acidification of the aqueous solution with 2N hydrochloric acid the separated precipitate was filtered off under suction, washed with water and dried at 60° C. in a drying oven overnight. The crude product was dissolved in 50 ml of dimethoxyethane, treated with 30 ml of diazomethane solution and stirred at room temperature for 1 hour. An excess of diazomethane was destroyed by adding acetic acid. The reaction mixture was concentrated and chromatographed on silica gel with ethyl acetate/hexane/methylene chloride. There was obtained dimethyl (E)-stilbene-3,4'-dicarboxylate, MS: m/z 296 (M$^+$).

C. A solution of 2.2 g of dimethyl (E)-stilbene-3,4'-dicarboxylate in 25 ml of dimethoxymethane and 12 ml of methanol was treated with 10 ml of 2M sodium hydroxide solution and heated under reflux for 18 hours. The reaction solution was concentrated. The aqueous residue was again diluted with water and acidified to pH 1 with 2N hydrochloric acid. The precipitate was filtered off under suction, rinsed with ice-water and dried at 60° C. overnight in a drying oven. There was obtained (E)-stilbene-3,4'-dicarboxylic acid as a light coloured powder, MS: m/z 268 (M$^+$).

D. Reaction of (E)-stilbene-3,4'-dicarboxylic acid and D-glucamine as described under Example 3.A. gave (E)-stilbene-3,4'-dicarboxylic acid bis-D-glucit-1-ylamide, $[\alpha]_D^{20}$ −1.6° (c 0.5; DMSO), MS: m/z 595.4 ([M+H]$^+$).

E. Sulfation of (E)-stilbene-3,4'-dicarboxylic acid bis-D-glucit-1-ylamide as described under Example 2.B. gave (E)-stilbene-3,4'-dicarboxylic acid bis-(2,3,4,5,6-penta-O-sulfo-D-glucit-1-ylamide) decasodium salt, $[\alpha]_D^{20}$ −6.6° (c 0.5; water), MS: m/z 1615.0 (reconstructed M).

Example 73

A. Reaction of 3-bromobenzaldehyde with (3-bromobenzyl)-triphenylphosphonium bromide as described under Example 72.A. gave (E)-3,3'-dibromostilbene as colourless crystals, MS: m/z 338 (M$^+$), as well as (Z)-3,3'-dibromostilbene as a colourless oil, MS: m/z 338 (M$^+$).

B. Reaction of (E)-3,3'-dibromostilbene as described under Example 72.B. gave dimethyl (E)-stilbene-3,3'-dicarboxylate, MS: m/z 296 (M$^+$).

C. Reaction of dimethyl (E)-stilbene-3,3'-dicarboxylate as described under Example 72.C. gave (E)-stilbene-3,3'-dicarboxylic acid, MS: m/z 268 (M$^+$).

D. Reaction of (E)-stilbene-3,3'-dicarboxylic acid and D-glucamine as described under Example 3.A. gave (E)-stilbene-3,3'-dicarboxylic acid bis-D-glucit-1-ylamide, $[\alpha]_D^{20}$ −3.2° (c 0.5; DMSO), MS: m/z 595,5 ([M+H]$^+$).

E. Sulfation of (E)-stilbene-3,3'-dicarboxylic acid bis-D-glucit-1-ylamide as described under Example 2.B. gave (E)-stilbene-3,3'-dicarboxylic acid bis-(2,3,4,5,6-penta-O-sulfo-D-glucit-1-ylamide) decasodium salt, $[\alpha]_D^{20}$ −7.8° (c 0.5; water), MS: m/z 1616.0 (reconstructed M).

Example 74

A. Reaction of 4-bromobenzaldehyde with (2-bromo-benzyl)-triphenylphosphonium bromide as described under Example 72.A. gave (E)-2,4'-dibromostilbene as colourless crystals, MS: m/z 338 (M$^+$), as well as (Z)-2,4'-dibromostilbene as a colourless oil, MS: m/z 338 (M$^+$).

B. Reaction of (E)-2,4'-dibromostilbene as described under Example 72.B. gave dimethyl (E)-stilbene-2,4'-dicarboxylate, MS: m/z 296 (M$^+$).

C. Reaction of dimethyl (E)-stilbene-2,4'-dicarboxylate as described under Example 72.C. gave (E)-stilbene-2,4'-dicarboxylic acid, MS: m/z 268 (M$^+$).

D. Reaction of (E)-stilbene-2,4'-dicarboxylic acid and D-glucamine as described under Example 3.A. gave (E)- stilbene-2,4'-dicarboxylic acid bis-D-glucit-1-ylamide, $[\alpha]_D^{20}$ −11.8° (c 0.5; DMSO), MS: m/z 595.4 ([M+H]$^+$).

E. Sulfation of (E)-stilbene-2,4'-dicarboxylic acid bis-D-glucit-1-ylamide as described under Example 2.B. gave (E)-stilbene-2,4'-dicarboxylic acid bis-(2,3,4,5,6-penta-O-sulfo-D-glucit-1-ylamide) decasodium salt, $[\alpha]_D^{20}$ −7.4° (c 0.5; water), MS: m/z 1615.0 (reconstructed M).

Example 75

A. Reaction of 3-bromobenzaldehyde with (2-bromobenzyl)-triphenylphosphonium bromide as described under Example 72.A. gave (E)-2,3'-dibromstilbene as colourless crystals, MS: m/z 338 (M$^+$), as well as (Z)-2,3'-dibromstilbene as a colourless oil, MS: m/z 338 (M$^+$).

B. Reaction of (E)-2,3'-dibromstilbene as described under Example 72.B. gave dimethyl (E)-stilbene-2,3'-dicarboxylate, MS: m/z 296 (M$^+$).

C. Reaction of dimethyl (E)-stilbene-2,3'-dicarboxylate as described under Example 72.C. gave (E)-stilbene-2,3'-dicarboxylic acid, MS: m/z 268 (M$^+$).

D. Reaction of (E)-stilbene-2,3'-dicarboxylic acid and D-glucamine as described under Example 3.A. gave (E)-stilbene-2,3'-dicarboxylic acid bis-D-glucit-1-ylamide, $[\alpha]_D^{20}$ −9.4° (c 0.5; DMSO), MS: m/z 595.4 ([M+H]$^+$).

E. Sulfation of (E)-stilbene-2,3'-dicarboxylic acid bis-D-glucit-1-ylamide as described under Example 2.B. gave (E)-stilbene-2,3'-dicarboxylic acid bis-(2,3,4,5,6-penta-O-sulfo-D-glucit-1-ylamide) decasodium salt, $[\alpha]_D^{20}$ −9.6° (c 0.5; water), MS: m/z 1616.0 (reconstructed M).

Example 76

A. Reaction of 2-bromobenzaldehyde with (2-bromobenzyl)-triphenylphosphonium bromide as described under Example 72.A. gave (Z)-2,2'-dibromstilbene as a colourless oil, MS: m/z 338 (M$^+$).

B. Reaction of (Z)-2,2'-dibromstilbene as described under Example 72.B. gave dimethyl (Z)-stilbene-2,2'-dicarboxylate, MS: m/z 296 (M$^+$).

C. Reaction of dimethyl (Z)-stilbene-2,2'-dicarboxylate as described under Example 72.C. gave (Z)-stilbene-2,2'-dicarboxylic acid, MS: m/z 268 (M$^+$).

D. Reaction of (Z)-stilbene-2,2'-dicarboxylic acid and D-glucmine as described under Example 3.A. gave (Z)-stilbene-2,2'-dicarboxylic acid bis-D-glucit-1-ylamide, $[\alpha]_D^{20}$ −8.2° (c 0.5; DMSO), MS: m/z 595.5 ([M+H]$^+$).

E. Sulfation of (Z)-stilbene-2,2'-dicarboxylic acid bis-D-glucit-1-ylamide as described under Example 2.B. gave (Z)-stilbene-2,2'-dicarboxylic acid bis-(2,3,4,5,6-penta-O-sulfo-D-glucit-1-ylamide) decasodium salt, $[\alpha]_D^{20}$ −15.4° (c 0.5; water), MS: m/z 1615.0 (reconstructed M).

Example 77

A. Reaction of (Z)-3,4'-dibromstilbene as described under Example 72.B. gave dimethyl (Z)-stilbene-3,4'-dicarboxylate, MS: m/z 296 (M$^+$).

B. Reaction of dimethyl (Z)-stilbene-3,4'-dicarboxylate as described under Example 72.C. gave (Z)-stilbene-3,4'-dicarboxylic acid, MS: m/z 268 (M$^+$).

C. Reaction of (Z)-stilbene-3,4'-dicarboxylic acid and D-glucamine as described under Example 3.A. gave (Z)-stilbene-3,4'-dicarboxylic acid bis-D-glucit-1-ylamide, $[\alpha]_D^{20}$ −8.4° (c 0.5; DMSO), MS: m/z 595.5 ([M+H]$^+$).

D. Sulfation of (Z)-stilbene-3,4'-dicarboxylic acid bis-D-glucit-1-ylamide as described under Example 2.B. gave (Z)-stilbene-3,4'-dicarboxylic acid bis-(2,3,4,5,6-penta-O-sulfo-D-glucit-1-ylamide) decasodium salt, $[\alpha]_D^{20}$ −6.2° (c 0.5; water), MS: m/z 1616.0 (reconstructed M).

Example 78

A. Reaction of (Z)-3,3'-dibromstilbene as described under Example 72.B. gave dimethyl (Z)-stilbene-3,3'-dicarboxylate, MS: m/z 296 (M$^+$).

B. Reaction of dimethyl (Z)-stilbene-3,3'-dicarboxylate as described under Example 72.C. gave (Z)-stilbene-3,3'-dicarboxylic acid, MS: m/z 268 (M$^+$).

C. Reaction of (Z)-stilbene-3,3'-dicarboxylic acid and D-glucamine as described under Example 3.A. gave (Z)-stilbene-3,3'-dicarboxylic acid bis-D-glucit-1-ylamide, $[\alpha]_D^{20}$ −9.4° (c 0.5; DMSO), MS: m/z 595.4 ([M+H]$^+$).

D. Sulfation of (Z)-stilbene-3,3'-dicarboxylic acid bis-D-glucit-1-ylamide as described under Example 2.B. gave (Z)-stilbene-3,3'-dicarboxylic acid bis-(2,3,4,5,6-penta-O-sulfo-D-glucit-1-ylamide) decasodium salt, $[\alpha]_D^{20}$ −8.6° (c 0.5; water), MS: m/z 1615.0 (reconstructed M).

Example 79

A. Reaction of (Z)-2,3'-dibromstilbene as described under Example 72.B. gave dimethyl (Z)-stilbene-2,3'-dicarboxylate, MS: m/z 296 (M$^+$).

B. Reaction of dimethyl (Z)-stilbene-2,3'-dicarboxylate as described under Example 72.C. gave (Z)-stilbene-2,3'-dicarboxylic acid, MS: m/z 268 (M$^+$).

C. Reaction of (Z)-stilbene-2,3'-dicarboxylic acid and D-glucamine as described under Example 3.A. gave (Z)-stilbene-2,3'-dicarboxylic acid bis-D-glucit-1-ylamide, $[\alpha]_D^{20}$ −6.0° (c 0.5; DMSO), MS: m/z 595.4 ([M+H]$^+$).

D. Sulfation of (Z)-stilbene-2,3'-dicarboxylic acid bis-D-glucit-1-ylamide as described under Example 2.B. gave (Z)-stilbene-2,3'-dicarboxylic acid bis-(2,3,4,5,6-penta-O-sulfo-D-glucit-1-ylamide) decasodium salt, $[\alpha]_D^{20}$ −11.0° (c 0.5; water), MS: m/z 1615.0 (reconstructed M).

Example 80

Hydrogenation of (E)-stilbene-3,4'-dicarboxylic acid bis-(2,3,4,5,6-penta-O-sulfo-D-glucit-1-ylamide) decasodium salt (see Example 72) as described under Example 10. gave 3,4'-ethylenedibenzoic acid bis-(2,3,4,5,6-penta-O-sulfo-D-glucit-1-ylamide) decasodium salt, $[\alpha]_D^{20}$ −6.0° (c 0.5; water), MS: m/z 1617.5 (reconstructed M).

Example 81

Hydrogenation of (E)-stilbene-2,4'-dicarboxylic acid bis-(2,3,4,5,6-penta-O-sulfo-D-glucit-1-ylamide) decasodium salt (see Example 74) as described under Example 10. gave 2,4'-ethylenedibenzoic acid bis-(2,3,4,5,6-penta-O-sulfo-D-glucit-1-ylamide) decasodium salt, $[\alpha]_D^{20}$ −8.4° (c 0.5; water), MS: m/z 1616.8 (reconstructed M).

Example 82

Hydrogenation of (E)-stilbene-2,3'-dicarboxylic acid bis-(2,3,4,5,6 -penta-O-sulfo-D-glucit-1-ylamide) decasodium salt (see Example 75) as described under Example 10 gave 2,3'-ethylenedibenzoic acid bis-(2,3,4,5,6-penta-O-sulfo-D-glucit-1-ylamide) decasodium salt, $[\alpha]_D^{20}$ −10.0° (c 0.5; water), MS: m/z 1617.2 (reconstructed M).

Example 83

Hydrogenation of (Z)-stilbene-2,2'-dicarboxylic acid bis-(2,3,4,5,6-penta-O-sulfo-D-glucit-1-ylamide) decasodium salt (see Example 76) as described under Example 10 gave 2,2'-ethylenedibenzoic acid bis-(2,3,4,5,6-penta-O-sulfo-D-glucit-1-ylamide) decasodium salt, $[\alpha]_D^{20}$ −11.0° (c 0.5; water), MS: m/z 1617.2 (reconstructed M).

Example 84

Hydrogenation of (E)-stilbene-3,3'-dicarboxylic acid bis-(2,3,4,5,6-penta-O-sulfo-D-glucit- 1-ylamide) decasodium salt (see Example 73) as described under Example 10. gave 3,3'-ethylenedibenzoic acid bis-(2,3,4,5,6-penta-O-sulfo-D-glucit-1-ylamide) decasodium salt, $[\alpha]_D^{20}$ −4.2° (c 0.5; water), MS: m/z 1617.6 (reconstructed M).

Example 85

A. A solution of 55.3 g of methyl 3-chloro-4-methylbenzoate in 1 l of carbon tetrachloride was treated with 53.2 g of N-bromosuccinimide and 0.1 g of dibenzoyl peroxide and heated at reflux for 2 hours under a 150 W bulb. Precipitated succinimide was filtered off from the cooled reaction solution. The filtrate was concentrated and filtered over silica gel with carbon tetrachloride/ether. The eluate was evaporated and dried in a vacuum. A solution of this crude product in 750 ml of benzene was treated with 83 g of triphenylphosphine and heated under reflux for 4 hours, whereby the product separated. The suspension was cooled to about 15° C. and suction filtered. The product was washed with benzene and ether and dried at 50° C. in a vacuum. There was obtained (2-chloro-4-methoxycarbonylbenzyl)-triphenylphosphonium bromide, MS: m/z 445.3 (M⁺).

B. A suspension of 52.6 g of (2-chloro-4-methoxycarbonylbenzyl)-triphenylphosphonium bromide in 500 ml of tetrahydrofuran was treated at 0° C. with 115 ml of 2% methanolic sodium methylate solution. Then, a solution of 16.4 g of methyl 4-formylbenzoate was added dropwise within 10 minutes and the mixture was stirred at room temperature for 1 hour. The suspension was filtered over Dicalite and the filtrate was evaporated. The residue was chromatographed using ethyl acetate/hexane/methylene chloride and gave dimethyl (Z)-2-chlorostilbene-4,4'-dicarboxylate, MS: m/z 330 (M⁺), and dimethyl (E)-2-chlorostilbene-4,4'-dicarboxylate as colourless crystals, m.p. 134°–135° C., MS: m/z 330 (M⁺).

C. Reaction of dimethyl (E)-2-chlorostilbene-4,4'-dicarboxylate as described under Example 72.C. gave (E)-2-chlorostilbene-4,4'-dicarboxylic acid, MS: m/z 302 (M⁺).

D. Reaction of (E)-2-chlorostilbene-4,4'-dicarboxylic acid and D-glucamine as described under Example 3.A. gave (E)-2-chlorostilbene-4,4'-dicarboxylic acid bis-D-glucit-1ylamide, $[\alpha]_D^{20}$ −2.0° (c, 0.5; DMSO), MS: m/z 630.5 ([M+H]⁺).

E. Sulfation of (E)-2-chlorostilbene-4,4'-dicarboxylic acid bis-D-glucit-1-ylamide as described under Example 2.B. gave (E)-2-chlorostilbene-4,4'-dicarboxylic acid bis-(2,3,4,5,6-penta-O-sulfo-D-glucit-1-ylamide) decasodium salt, $[\alpha]_D^{20}$ −5.2° (c 0.5; water), MS: m/z 1650.0 (reconstructed M).

Example 86

A. Reaction of dimethyl (Z)-2-chlorostilbene-4,4'-dicarboxylate as described under Example 72.C. gave (Z)-2-chlorostilbene-4,4'-dicarboxylic acid, MS: m/z 302 (M⁺).

B. Reaction of (Z)-2-chlorostilbene-4,4'-dicarboxylic acid and D-glucamine as described under Example 3.A. gave (Z)-2-chlorostilbene-4,4'-dicarboxylic acid bis-D-glucit-1-ylamide, $[\alpha]_D^{20}$ −4.4° (c 0.5; DMSO), MS: m/z 629.6 ([M+H]⁺).

C. Sulfation of (Z)-2-chlorostilbene-4,4'-dicarboxylic acid bis-D-glucit-1-ylamide as described under Example 2.B. gave (Z)-2-chlorostilbene-4,4'-dicarboxylic acid bis-(2,3,4,5,6-penta-O-sulfo-D-glucit-1-ylamide) decasodium salt, $[\alpha]_D^{20}$ −4.2° (c 0.5; water), MS: m/z 1659.5 (reconstructed M).

Example 87

A. Reaction of (2-bromo-4-methoxycarbonylbenzyl)-triphenylphosphonium bromide with methyl 4-formylbenzoate as described in Example 85.B. gave crystalline dimethyl (Z)-2-bromostilbene-4,4'-dicarboxylate, MS: m/z 374 (M⁺), and dimethyl (E)-2-bromostilbene-4,4'-dicarboxylate, MS: m/z 374 (M⁺).

B. Reaction of dimethyl (E)-2-bromostilbene-4,4'-dicarboxylate as described under Example 72.C. gave (E)-2-bromostilbene-4,4'-dicarboxylic acid, MS: m/z 346 (M⁺).

C. Reaction of (E)-2-bromostilbene-4,4'-dicarboxylic acid and D-glucamine as described under Example 3.A. gave (E)-2-bromostilbene-4,4'-dicarboxylic acid bis-D-glucit-1-ylamide, $[\alpha]_D^{20}$ −2.4° (c 0.5; DMSO), MS: m/z 695.5 ([M+H]⁺).

D. Sulfation of (E)-2-bromostilbene-4,4'-dicarboxylic acid bis-D-glucit-1-ylamide as described under Example 2.B. gave (E)-2-bromostilbene-4,4'-dicarboxylic acid bis-(2,3,4,5,6-penta-O-sulfo-D-glucit-1-ylamide) decasodium salt $[\alpha]_D^{20}$ −4.2° (c 0.5; water), MS: m/z 1694.0 (reconstructed M).

Example 88

A. Reaction of dimethyl (Z)-2-bromostilbene-4,4'-dicarboxylate as described under Example 72.C. gave (Z)-2-bromostilbene-4,4'-dicarboxylic acid, MS: m/z 346 (M⁺).

B. Reaction of (Z)-2-bromostilbene-4,4'-dicarboxylic acid and D-glucamine as described under Example 3.A. gave (Z)-2-bromostilbene-4,4'-dicarboxylic acid-bis-D-glucit-1-ylamide, $[\alpha]_D^{20}$ −2.4° (c 0.5; DMSO), MS: m/z 673.6 ([M+H]⁺).

C. Sulfation of (Z)-2-bromostilbene-4,4'-dicarboxylic acid bis-D-glucit-1-ylamide as described under Example 2.B. gave (Z)-2-bromostilbene-4,4'-dicarboxylic acid bis-(2,3,4,5,6-penta-O-sulfo-D-glucit-1-ylamide) decasodium salt, $[\alpha]_D^{20}$ −2.8° (c 0.5; water), MS: m/z (reconstructed M).

Example 89

A. Reaction of 4-(2,3,4,5,6-penta-O-acetyl-D-glucit-1-ylamin)-3-nitrobenzoic acid with (E)-4,4'-diaminostilbene as described under Example 68.B. gave (E)-4,4'-bis-(2,3,4,5,6-penta-O-acetyl-D-glucit-1-ylamino)- 3,3'-dinitro-N,N'-stilbene-4,4'-diyl-dibenzamide, $[\alpha]_D^{20}$ −10.4° (c 0.5; DMSO), MS: m/z 1287.4 ([M+Na]⁺).

B. Reaction of (E)-4,4'-bis-(2,3,4,5,6-penta-O-acetyl-D-glucit-1-ylamino)- 3,3'-dinitro-N,N'-stilbene-4,4'-diyl-dibenzamide as described under Example 68.C. gave (E)-4,4'-bis-D-glucit-1-ylamino-3,3'-dinitro-N,N'-stilbene- 4,4'-diyl-dibenzamide, $[\alpha]_D^{20}$ +25.0° (c 0.5; DMSO), MS: m/z 867.4 ([M+Na]⁺).

C. Reaction of (E)-4,4'-bis-D-glucit-1-ylamino-3,3'-dinitro-N,N'-stilbene-4,4'-diyl-dibenzamide as described under Example 67.B. gave (E)-4,4'-bis-( 2,3,4,5,6-penta-O-sulfo-D-glucit-1-ylamino)-3,3'-dinitro-N,N'-stilbene- 4,4'-diyl-dibenzamide decasodium salt as a yellow-orange powder, $[\alpha]_D^{20}$ +5.8° (c 0.5; water), MS: m/z 1887.0 (reconstructed M).

Example 90

A. A suspension of 1.69 g of (Z)-stilbene-4,4'-dicarboxylic acid in 40 ml of tetrahydrofuran, 40 ml of acetonitrile and 1.43 ml of N-methylmorpholine was treated with 2.22 g of 2-chloro-4,6-dimethoxy-1,3,5-triazine and stirred at room temperature for 2 hours. After the addition of 2.3 g of 1-amino-1-deoxy-D-mannitol the mixture was stirred at room temperature for 19 hours. Separated crystals were filtered off and acetylated with acetic anhydride in pyridine. The reaction mixture was concentrated and chromatographed over silica gel. The purified product was deacetylated as described under Example 1.A. and gave (Z)-stilbene-4,4'-dicarboxylic acid bis-D-mannit-1-ylamide, $[\alpha]_D^{20}$ +3.5° (c 0.2; DMF), MS: m/z 595.5 ($[M+H]^+$).

B. Reaction of (Z)-stilbene-4,4'-dicarboxylic acid bis-D-mannit-1-ylamide as described under Example 2.B. gave (Z)-stilbene-4,4'-dicarboxylic acid bis-(2,3,4,5,6-penta-O-sulfo-D-mannit-1-ylamide) decasodium salt, $[\alpha]_D^{20}$ +19.5° (c 0.2; water), MS: m/z 1614 (reconstructed M).

Example 91

A. Reaction of (Z)-stilbene-4,4'-dicarboxylic acid with 1-amino-1-deoxy-D-galactitol as described under Example 90.A. gave (Z)-stilbene-4,4'-dicarboxylic acid bis-D-galactit-1-ylamide, MS: m/z 595.4 ($[M+H]^+$).

B. Reaction of (Z)-stilbene-4,4'-dicarboxylic acid bis-D-galactit-1-ylamide as described under Example 2.B. gave (Z)-stilbene-4,4'-dicarboxylic acid bis-(2,3,4,5,6-penta-O-sulfo-D-galactit-1-ylamide) decasodium salt, $[\alpha]_D^{20}$ –14.0° (c 0.2; water), MS: m/z 1615 (reconstructed M).

Example 92

A. Reaction of (Z)-stilbene-4,4'-dicarboxylic acid with 1-amino-1-deoxy-D-arabinitol as described under Example 90.A. gave (Z)-stilbene-4,4'-dicarboxylic acid bis-D-arabinit-1-ylamide, MS: m/z 557.4 ($[M+Na]^+$).

B. Reaction of (Z)-stilbene-4,4'-dicarboxylic acid bis-D-arabinit-1-ylamide as described under Example 2.B. gave (Z)-stilbene-4,4'-dicarboxylic acid bis-(2,3,4,5,6-penta-O-sulfo-D-arabinit-1-ylamide) octasodium salt, $[\alpha]_D^{20}$ +25.5° (c 0.2; water), MS: m/z 1350.0 (reconstructed M).

Example 93

A. Reaction of (Z)-stilbene-4,4'-dicarboxylic acid with 1-amino-1-deoxy-L-rhamnitol as described under Example 90.A. gave (Z)-stilbene-4,4'-dicarboxylic acid bis-L-rhamnit-1-ylamide, MS: m/z 563.7 ($[M+H]^+$).

B. Reaction of (Z)-stilbene-4,4'-dicarboxylic acid bis-L-rhamnit-1-ylamide as described under Example 2.B. gave (Z)-stilbene-4,4'-dicarboxylic acid bis-(2,3,4,5,6-penta-O-sulfo-L-rhamnit-1-ylamide) octasodium salt, $[\alpha]_D^{20}$ –21.0° (c 0.2; water), MS: m/z 1379.0 (reconstructed M).

Example 94

A. A suspension of 2.0 g of 1-amino-1-deoxy-D-mannitol in 20 ml of dimethylformamide was treated with toluylene-2,6-diisocyanate and stirred at room temperature for 6 hours. Direct acetylation was carried out by adding acetic anhydride and pyridine. The reaction mixture was concentrated and chromatographed over silica gel. Pure product fractions were concentrated, dissolved in methanol/dioxane and treated with 2% methanolic sodium methylate solution. After 18 hours at room temperature resulting crystals were filtered off under suction, washed with methanol and dried. There resulted 3,3'-di-D-mannit-1-yl-1,1'-(toluen-2,6-diyl)-diurea, MS: m/z 537.6 ($[M+H]^+$).

B. Reaction of 3,3'-di-D-mannit-1-yl-1,1'-(toluene-2,6-diyl)-diurea as described under Example 2.B. gave 3,3'-bis-(2,3,4,5,6-penta-O-sulfo-D-mannit- 1-yl)-1,1'-(toluene-2,6-diyl)-diurea decasodium salt, $[\alpha]_D^{20}$ +16.0° (c 0.2; water), MS: m/z 1556.0 (reconstructed M).

Example 95

A. Reaction of 1-amino-1-deoxy-D-galactitol with toluylene-2,6-diisocyanate as described under Example 94.A. gave 3,3'-di-D-galactit-1 -yl-1,1'-(toluene-2,6-diyl)-diurea, MS: m/z 537.5 ($[M+H]^+$).

B. Reaction of 3,3'-di-D-galactit-1-yl-1,1'-(toluene-2,6-diyl)-diurea as described under Example 2.B. gave 3,3'-bis-(2,3,4,5,6-penta-O-sulfo-D-galactit- 1-yl)-1,1'-(toluene-2,6-diyl)-diurea decasodium salt, $[\alpha]_D^{20}$ –3.0° (c 0.2; water), MS: m/z 1556.0 (reconstructed M).

Example 96

A. Reaction of 1-amino-1-deoxy-D-arabinitol with toluylene-2,6-diisocyanate as described under Example 94.A. gave 3,3'-di-D-arabinit-1-yl-1,1'-(toluene-2,6-diyl)-diurea, MS: m/z 499.5 ($[M+Na]^+$).

B. Reaction of 3,3'-di-D-arabinit-1-yl-1,1'-(toluene-2,6-diyl)-diurea as described under Example 2.B. gave 3,3'-bis-(2,3,4,5,6-penta-O-sulfo-D-arabinit- 1-yl)-1,1'-(toluene-2,6-diyl)-diurea octasodium salt, $[\alpha]_D^{20}$ +14.0° (c 0.2; water), MS: m/z 1293.0 (reconstructed M).

Example 97

A. Reaction of 1-amino-1-deoxy-L-rhamnitol with toluylene-2,6-diisocyanate as described under Example 94.A. gave 3,3'-di-L-rhamnit-1-yl-1,1'-(toluene-2,6-diyl)-diurea, MS: m/z 527 ($[M+Na]^+$).

B. Reaction of 3,3'-di-L-rhamnit-1-yl-1,1'-(toluene-2,6-diyl)-diurea as described under Example 2.B. gave 3,3'-bis-(2,3,4,5,6-penta-O-sulfo-L-rhamnit- 1-yl)-1,1'-(toluene-2,6-diyl)-diurea octasodium salt, $[\alpha]_D^{20}$ –15.0° (c 0.2; water), MS: m/z 1321.0 (reconstructed M).

Example 98

Production of tablets, pellets and injection solution.
A. Tablets

| | | |
|---|---|---|
| 1 | Compound of formula I | 500 mg |
| 2 | Anhydrous lactose | 150 mg |
| 3 | Microcrystalline cellulose | 150 mg |
| 4 | Polyvinylpyrrolidone | 40 mg |
| 5 | Talc | 50 mg |

-continued

| 6 | Magnesium stearate | 10 mg |
|---|---|---|
|   | Tablet weight | 900 mg |

Ingredients 1–4 are sieved and mixed. This mixture is granulated with demineralized water and the dried granulate is mixed with ingredients 5 and 6. The mixture is pressed to tablets of suitable form.

B. Pellets

| 1 | Compound of formula I | 500 mg |
|---|---|---|
| 2 | Microcrystalline cellulose | 200 mg |
| 3 | PRIMOJEL | 70 mg |
| 4 | Flavour powder | 10 mg |
| 5 | Talc | 20 mg |

Mixed and sieved ingredients 1–3 are moistened sufficiently with demineralized water and pressed by means of an extruder through a suitable perforated disc. The extrudate is transferred to a pelleting plate, rounded-off to beadlets and subsequently dried. The mixture is treated with sieved ingredients 4 and 5 and filled into paper sachets (or similar).

C. Injection solution

For the production of an injection solution, 50 mg of a compound of formula I and 0.5 mg of Tris buffer are dissolved in water to a final injection volume of 1 ml and the pH value is adjusted to 7.4. The solution is sterile filtered, dispensed into ampules and autoclaved.

What is claimed is:

1. Compounds of the formula

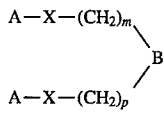

wherein

A is a residue of a sugar alcohol or of a derivative thereof that lacks a 1-hydroxy group, or a tris-(hydroxymethyl)methyl residue, with at least one hydroxy group of the residue A being esterified with sulfuric acid;

X is —NR$^1$CO—; —NHCONH—; —NHCSNH—; —NHSO$_2$—; —NR$^1$— or —O—;

m and p are each independently 0 or 1;

R$^1$ is hydrogen, lower-alkyl or hydroxy-lower-alkyl;

B is a system of conjugated multiple bonds;

and salts thereof.

2. The compounds of claim 1 wherein the system of conjugated multiple bonds B is a system of conjugated double bonds.

3. The compounds of claim 2 wherein X is —NR$^1$CO—, —NHCONH—, —NHCSNH—, —NHSO$_2$— or —O—; A is a residue —(CHR$^2$)$_n$CH$_2$R$^2$; n is a whole number of 1–5; R$^2$ is H, —OSO$_3$H or OZ; Z is a protecting group and at least one residue R$^2$ is —OSO$_3$H.

4. The compounds of claim 3, wherein the system of conjugated multiple bonds B comprises a polyene or polyyne hydrocarbon residue having 2–8 conjugated multiple bonds.

5. The compounds of claim 4, wherein A is a residue derived from glucitol, galactitol, mannitol, gulitol, arabinitol, ribitol and xylitol.

6. The compounds of claim 5, wherein A is derived from L-rhamnitol.

7. The compounds of claim 2, wherein the system of conjugated double bonds is an aromatic ring system.

8. The compounds of claim 7, wherein the aromatic ring system is phenylene, phenylene substituted by lower-alkyl, naphthylene, fluorenylene, or a residue selected from the group consisting of

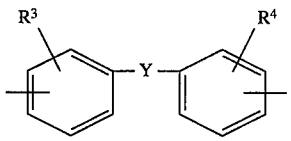

(a)

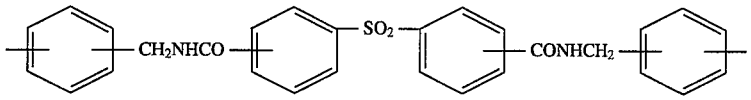

(b)

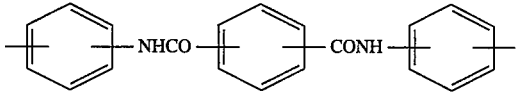

(c)

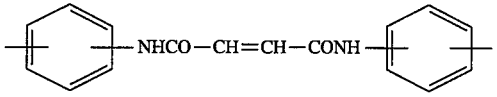

(d)

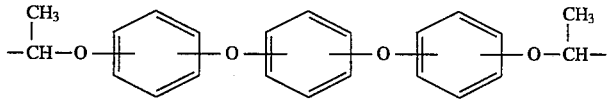

(e)

-continued
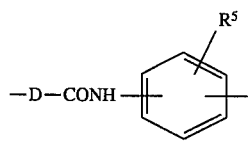 (f)
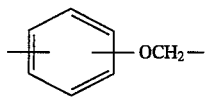 (g)
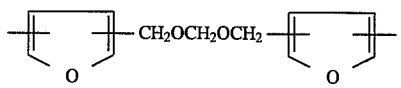 (h)
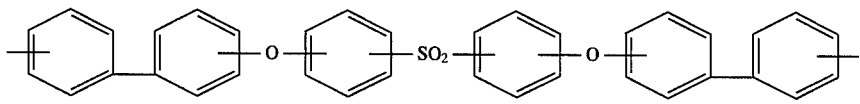 (i)
(j)
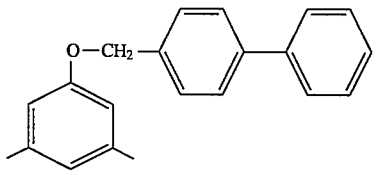
(k)
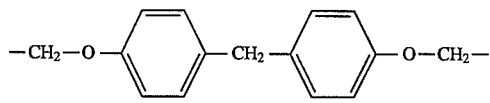
(l)
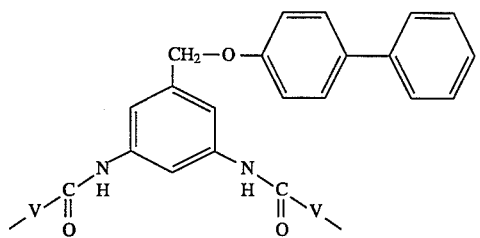
(m)
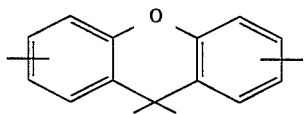
(n)
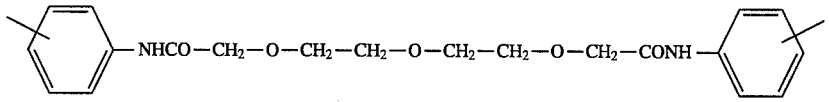
(o)
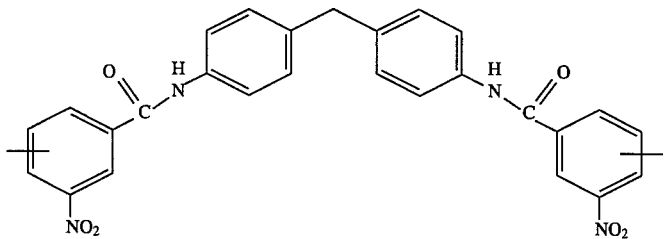
(p)
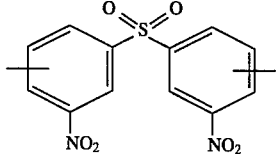

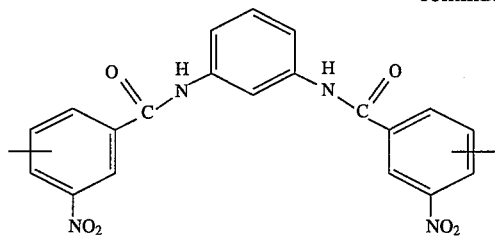
(q)

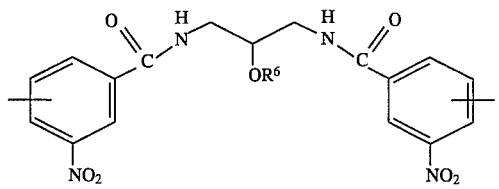
(r)

and

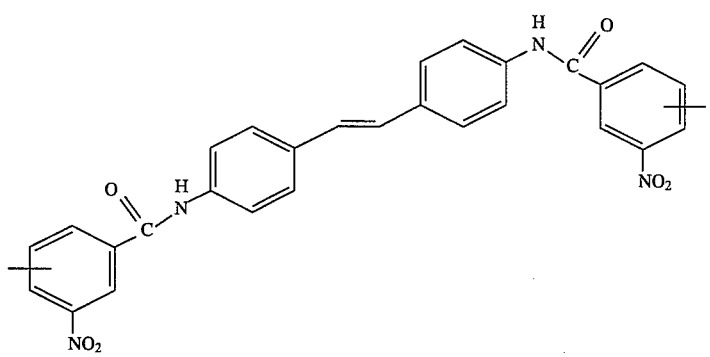
(s)

wherein Y is a carbon-carbon bond, —O—, —CO—, —CH$_2$—, —CH$_2$CH$_2$—, —C≡C—, —CH(O)CH—, —CH=CH—, —SO$_2$—, —C(CF$_3$)$_2$—, —CONR$^1$—, —NHCONH—, —NHCOCONH—, phenylene or phenylenedioxy; R$^1$ is hydrogen, lower alkyl or hydroxy-lower-alkyl; R$^3$ and R$^4$ are hydrogen, lower-alkyl, lower-alkoxy, halogen or —SO$_3$H; R$^5$ is lower-alkoxy-lower-alkoxy, phenoxy or phenoxy substituted by halogen; R$^6$ is hydrogen or SO$_3$H, D is —CH$_2$CH$_2$— or —CH=CH— and V is —CH=CH—, —CH$_2$CH$_2$— or a single bond.

9. A compound selected from the group consisting of:
(Z)-Butenedioic acid (Z)-[3-biphenyl-4-yloxymethyl-5-[3-(2,3,4,5,6-penta-O-sulfo-D-glucit-1-ylcarbamoyl)-acryloylamino]-phenylamide]-(2,3,4,5,6-penta-O-sulfo-D-glucit-1-yl)-amide decasodium salt,
(E)-2-chlorostilbene-4,4'-dicarboxylic acid bis-(2,3,4,5,6-penta-O-sulfo-D-glucit-1-ylamide) decasodium salt,
(Z)-stilbene-4,4'-dicarboxylic acid bis-(2,3,4,5,6-penta-O-sulfo-D-glucit-1-ylamide) decasodium salt,
(2E,4E,6E,8E,10E,12E,14E)-2,6,11,15-tetramethyl-hexadeca-2,4,6,8,10,12,14-heptaenedicarboxylic acid bis-(2,3,4,5,6-penta-O-sulfo-D-glucit-1-ylamide) decasodium salt,
4,4'-ethylene-dibenzoic acid bis-(2,3,4,5,6-penta-O-sulfo-D-glucit-1-ylamide) decasodium salt,
3,3'-bis-(2,3,4,5,6-penta-O-sulfo-D-glucit-1-yl)-1,1'-(toluene-2,6-diyl)-diurea decasodium salt,
4,4'-bis-(2,3,4,5,6-penta-O-sulfo-D-glucit-1-ylamino)-3,3'-dinitro-N,N'-(4,4'-methylene-diphenyl)-dibenzamide decasodium salt,
N,N'-bis-(2,3,4,5,6-penta-O-sulfo-D-glucit-1-yl)-2,2'-dinitro-4,4'-sulfonyldianiline decasodium salt,
(Z)-stilbene-4,4'-dicarboxylic acid bis-(2,3,4,5,6-penta-O-sulfo-L-rhamnit-1-ylamide) octasodium salt,
naphthalene-1,5-disulfonic acid bis-(2,3,4,5,6-penta-O-sulfo-D-glucit-1-ylamide) decasodium salt,
N,N'-bis-[4-(2,3,4,5-tetra-O-sulfo-D-arabinit-1-yloxy)-phenyl]-isophthalamide octasodium salt,
1,3-bis-[4-(2,3,4,5,6-penta-O-sulfo-D-galactit-6-yloxy)-phenyl]-urea decasodium salt,
N,N'-bis-[4-[3-(2,3,4,5,6-penta-O-sulfo-D-glucit-1-yl)-ureido]-phenyl]-isophthalamide decasodium salt,
9-oxo-9H-fluorene-2,7-dicarboxylic acid bis-[methyl-(2,3,4,5,6-penta-O-sulfo-D-glucit-1-yl)-amide] decasodium salt,
4,4'-methylene-dibenzoic acid bis-(2,3,4,5,6-penta-O-sulfo-D-glucit-1-ylamide) decasodium salt,
naphthalene-2,6-dicarboxylic acid bis-(2,3,4,5,6-penta-O-sulfo-D-glucit-1-ylamide) decasodium salt,
N,N'-bis-(2,3,4,5,6-penta-O-sulfo-D-glucit-1-yl)-isophthalamide decasodium salt,
N,N'-bis-[4-[3-(2,3,4,5,6-penta-O-sulfo-D-glucit-1-yl)-ureido]-phenyl]-fumaramide decasodium salt, and
4,4'-sulfonyl-dibenzoic acid bis-(2,3,4,5,6-penta-O-sulfo-D-glucit-1-ylamide) decasodium salt.

10. A method for inhibiting the migration and proliferation of smooth muscle cells in vascular walls comprising administering to a host a composition containing an effective amount of a compound of claim 1, or a salt thereof.

11. The method of claim 10, wherein said composition is administered parenterally.

12. The method of claim 11, wherein said composition is administered such that the patient receives a daily dose of from about 0.1 to 100 mg/kg body weight of said compound, or a salt thereof.

13. A method for inhibiting arteriosclerotic changes in the vascular wall comprising administering to a patient a composition containing a therapeutically effective amount of a compound of claim 9.

* * * * *